United States Patent [19]

Fischer

[11] Patent Number: 5,248,604
[45] Date of Patent: Sep. 28, 1993

[54] ENZYMATICALLY ACTIVE RECOMBINANT HUMAN ACETYLCHOLINESTERASE AND HOSTS AND VECTORS FOR EXPRESSION THEREOF

[75] Inventor: Meir Fischer, Rehovot, Israel

[73] Assignee: Bio-Technology General Corp., New York, N.Y.

[21] Appl. No.: 732,962

[22] Filed: Jul. 22, 1991

[51] Int. Cl.$^5$ .................. C12N 9/18; C12N 15/70
[52] U.S. Cl. .................. 435/197; 435/252.3; 435/252.33; 435/320.1
[58] Field of Search ............ 435/172.3, 197, 252.3, 435/320.1, 252.33; 536/27

[56] References Cited

U.S. PATENT DOCUMENTS 4,959,314  9/1990  Mark et al. .................. 435/69.1

FOREIGN PATENT DOCUMENTS 388906  9/1990  European Pat. Off. .

OTHER PUBLICATIONS

Rotundo (1988), J. Biol. Chem. 263(36):19398–19406.
Soreq et al., (Dec. 1990), Proc. Natl. Acad. Sci. U.S.A., vol. 87, pp. 9688–9692.
Towbin et al., (Sep. 1979), Proc. Natl. Acad. Sci. U.S.A., vol. 76, pp. 4350–4354.
Velan, B. et al., Cellular and Molecular Neurobiology 11, 143–156 (1991).

*Primary Examiner*—Richard A. Schwartz
*Assistant Examiner*—Philip W. Carter
*Attorney, Agent, or Firm*—John P. White

[57] ABSTRACT

The subject invention provides an enzymatically active nonglycosylated, recombinant, human acetylcholinesterase comprising at least one polypeptide characterized by an amino acid sequence which is substantially identical to the amino acid sequence of naturally-occurring human acetylcholinesterase. The subject invention additionally provides an enzymatically active recombinant human acetylcholinesterase comprising at least one polypeptide characterized by an amino acid sequence in which serine is substituted for cys 611 in the sequence of naturally-occurring human acetylcholinesterase and an enzymatically active recombinant human acetylcholinesterase comprising at least one polypeptide characterized by the presence of a methionine of the N-terminus of the amino acid sequence of naturally-occurring human acetylcholinesterase.

10 Claims, 17 Drawing Sheets

FIGURE 1
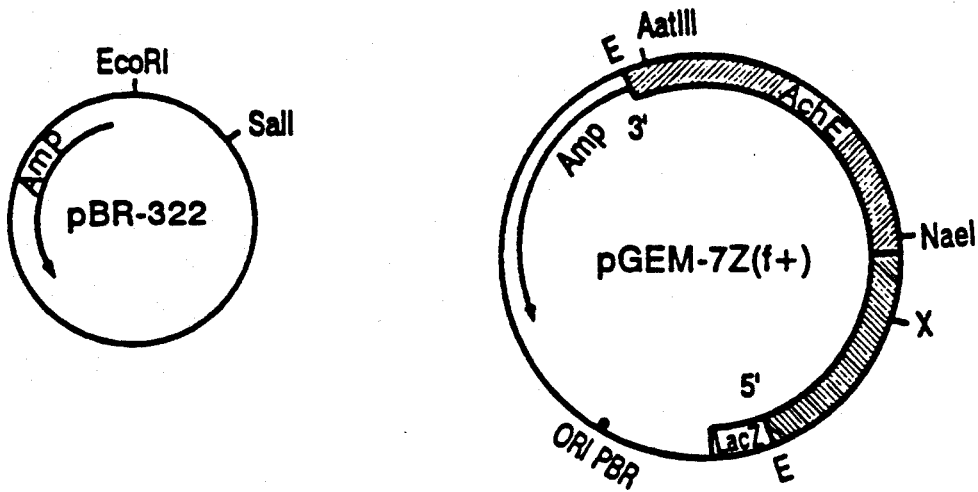
1. CLEAVE EcoRI+SalI
2. ISOLATE LARGE FRAGMENT
1. CLEAVE EcoRI
2. ISOLATE LARGE FRAGMENT
3. CLEAVE XhoI
4. ISOLATE 2650bp FRAGMENT
T4 LIGASE
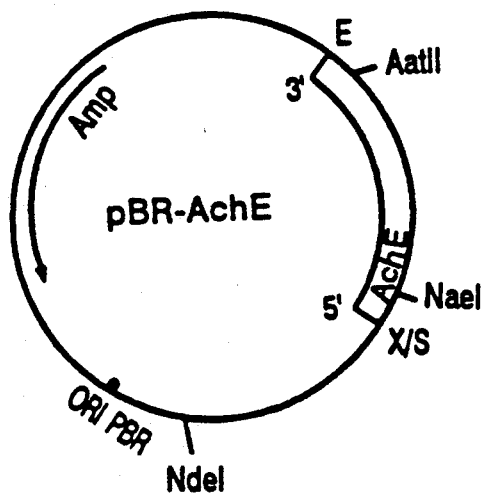

FIGURE 4A (SEQ ID NO: 1)

```
ATG AGG CCC CCG CAG TGT CTG CTG CAC ACG CCT TCC CTG GCT TCC CCA
 48
Met Arg Pro Pro Gln Cys Leu Leu His Thr Pro Ser Leu Ala Ser Pro
 1                       5                  10                 15

CTC CTT CTC CTC CTC TGG CTC CTG GGT GGA GTG GGG GCT GAG
 96
Leu Leu Leu Leu Leu Trp Leu Leu Gly Gly Val Gly Ala Glu
                    20                  25             30

GGC CGG GAG GAT GCA GAG CTG GTG ACG GTG CGT GGG GGC CGG CTG
144
Gly Arg Glu Asp Ala Glu Leu Val Thr Val Arg Gly Gly Arg Leu
                35                  40                  45

CGG GGC ATT CGC CTG AAG ACC CCC GGG GGC CCT GTC TCT GCT TTC CTG
192
Arg Gly Ile Arg Leu Lys Thr Pro Gly Gly Pro Val Ser Ala Phe Leu
             50                  55                  60

GGC ATC CCC TTT GCG GAG CCA CCC ATG GGA CCC CGT CGC TTT CTG CCA
240
Gly Ile Pro Phe Ala Glu Pro Pro Met Gly Pro Arg Arg Phe Leu Pro
 65                  70                  75                  80
```

FIGURE 4B (SEQ ID NO:1 CONTINUED)

```
CCG GAG CCC AAG CAG CCT TGG TCA GGG GTG GTA GAC GCT ACA ACC TTC
288
Pro Glu Pro Lys Gln Pro Trp Ser Gly Val Val Asp Ala Thr Thr Phe
        85                          90                      95

CAG AGT GTC TGC TAC CAA TAT GTG GAC ACC CTA TAC CCA GGT TTT GAG
336
Gln Ser Val Cys Tyr Gln Tyr Val Asp Thr Leu Tyr Pro Gly Phe Glu
            100                         105                     110

GGC ACC GAG ATG TGG AAC CCC AAC CGT GAG CTG AGC GAG GAC TGC CTG
384
Gly Thr Glu Met Trp Asn Pro Asn Arg Glu Leu Ser Glu Asp Cys Leu
        115                         120                     125

TAC CTC AAC GTG TGG ACA CCA TAC CCC CGG CCT ACA TCC CCC ACC CCT
432
Tyr Leu Asn Val Trp Thr Pro Tyr Pro Arg Pro Thr Ser Pro Thr Pro
        130                         135                     140

GTC CTC GTC TGG ATC TAT GGG GGT GGC TTC TAC AGT GGG GCC TCC TCC
480
Val Leu Val Trp Ile Tyr Gly Gly Gly Phe Tyr Ser Gly Ala Ser Ser
145                         150                     155                 160
```

FIGURE 4C (SEQ ID NO:1 CONTINUED)

```
TTG GAC GTG TAC GAT GGC CGC TTC TTG GTA CAG GCC GAG AGG ACT GTG
528
Leu Asp Val Tyr Asp Gly Arg Phe Leu Val Gln Ala Glu Arg Thr Val
                165                 170                 175

CTG GTG TCC ATG AAC TAC CGG GTG GGA GCC TTT GGC TTC CTG GCC CTG
576
Leu Val Ser Met Asn Tyr Arg Val Gly Ala Phe Gly Phe Leu Ala Leu
        180                 185                 190

CCG GGG AGC CGA GAG GCC CCG GGC AAT GTG CCG GGT CTC CTG GAT CAG AGG
624
Pro Gly Ser Arg Glu Ala Pro Gly Asn Val Pro Gly Leu Leu Asp Gln Arg
            195                 200                 205

CTG GCC CTG CAG TGG GTG CAG GAG AAC GTG GCA GCC TTC GGG GGT GAC
672
Leu Ala Leu Gln Trp Val Gln Glu Asn Val Ala Ala Phe Gly Gly Asp
                210                 215                 220

CCG ACA TCA GTG ACG CTG TTT GGG GAG AGC GCG GGA GCC GCC TCG GTG
720
Pro Thr Ser Val Thr Leu Phe Gly Glu Ser Ala Gly Ala Ala Ser Val
        225                 230                 235                 240
```

FIGURE 4D (SEQ ID NO:1 CONTINUED)

```
GGC ATG CAC CTG CTG TCC CCG CCC AGC CGG GGC CTG TTC CAC AGG GCC
768
Gly Met His Leu Leu Ser Pro Pro Ser Arg Gly Leu Phe His Arg Ala
        245                 250                 255

GTG CTG CAG AGC GGT GCC CCC AAT GGA CCC TGG GCC ACG GTG GGC ATG
816
Val Leu Gln Ser Gly Ala Pro Asn Gly Pro Trp Ala Thr Val Gly Met
        260                 265                 270

GGA GAG GCC CGT CGC AGG GCC ACG CAG CTG GCC CAC CTT GTG GGC TGT
864
Gly Glu Ala Arg Arg Arg Ala Thr Gln Leu Ala His Leu Val Gly Cys
        275                 280                 285

CCT CCA GGC GGC ACT GGT GGG AAT GAC ACA GAG CTG GTA GCC TGC CTT
912
Pro Pro Gly Gly Thr Gly Gly Asn Asp Thr Glu Leu Val Ala Cys Leu
        290                 295                 300

CGG ACA CGA CCA GCG CAG GTC CTG AAC CAC GAA TGG CAC GTG CTG
960
Arg Thr Arg Pro Ala Gln Val Leu Val Asn His Glu Trp His Val Leu
    305                 310                 315             320
```

FIGURE 4E (SEQ ID NO:1 CONTINUED)

```
CCT CAA GAA AGC GTC TTC CGG TTC TCC TTC GTG CCT GTG GTA GAT GGA
1008
Pro Gln Glu Ser Val Phe Arg Phe Ser Phe Val Pro Val Val Asp Gly
            325                     330                     335

GAC TTC CTC AGT GAC ACC CCA GAG GCC CTC ATC AAC GCG GGA GAC TTC
1056
Asp Phe Leu Ser Asp Thr Pro Glu Ala Leu Ile Asn Ala Gly Asp Phe
            340                     345                     350

CAC GGC CTG CAG GTG CTG GTG GGT GTG AAG GAT GAG GGC TCG TAT
1104
His Gly Leu Gln Val Leu Val Gly Val Lys Asp Glu Gly Ser Tyr
            355                     360                     365

TTT CTG GTT TAC GGG GCC CCA GGC TTC AGC AAA GAC AAC GAG TCT CTC
1152
Phe Leu Val Tyr Gly Ala Pro Gly Phe Ser Lys Asp Asn Glu Ser Leu
            370                     375                     380

ATC AGC CGG GCC GAG TTC CTG GCC GGG GTC GGG CGG GTG CCC CAG
1200
Ile Ser Arg Ala Glu Phe Leu Ala Gly Val Arg Val Gly Val Pro Gln
            385                     390                     395                     400
```

FIGURE 4F (SEQ ID NO:1 CONTINUED)

```
GTA AGT GAC CTG GCA GCC GAG GCT GTG GTC CTG CAT TAC ACA GAC TGG
1248
Val Ser Asp Leu Ala Ala Glu Ala Val Val Leu His Tyr Thr Asp Trp
                            405                             415

CTG CAT CCC GAG GAC CCG GCA CGC CTG AGG GAG GCC CTG AGC GAT GTG
1296
Leu His Pro Glu Asp Pro Ala Arg Leu Arg Glu Ala Leu Ser Asp Val
                 420                             430

GTG GGC GAC CAC AAT GTC GTG TGC CCC GTG GCC CAG CTG GCT GGG CGA
1344
Val Gly Asp His Asn Val Val Cys Pro Val Ala Gln Leu Ala Gly Arg
         435                             445

CTG GCT GCC CAG GGT GCC CGG GTC TAC GCC TAC GTC TTT GAA CAC CGT
1392
Leu Ala Ala Gln Gly Ala Arg Val Tyr Ala Tyr Val Phe Glu His Arg
450                             460

GCT TCC ACG CTC TCC TGG CCC CTG TGG ATG GGG GTG CCC CAC GGC TAC
1440
Ala Ser Thr Leu Ser Trp Pro Leu Trp Met Gly Val Pro His Gly Tyr
465                             475                         480
```

FIGURE 4G (SEQ ID NO:1 CONTINUED)

```
GAG ATC GAG TTC ATC TTT GGG ATC CCC CTG GAC CCC TCT CGA AAC TAC
1488
Glu Ile Glu Phe Ile Phe Gly Ile Pro Leu Asp Pro Ser Arg Asn Tyr
             485                       490                   495

ACG GCA GAG GAG AAA ATC TTC GCC CAG CGA CTG ATG CGA TAC TGG GCC
1536
Thr Ala Glu Glu Lys Ile Phe Ala Gln Arg Leu Met Arg Tyr Trp Ala
             500                       505                   510

AAC TTT GCC CGC ACA GGG GAT CCC AAT GAG CCC CGA GAC CCC AAG GCC
1584
Asn Phe Ala Arg Thr Gly Asp Pro Asn Glu Pro Arg Asp Pro Lys Ala
             515                       520                   525

CCA CAA TGG CCC CCG TAC ACG GCG GGG GCT CAG CAG TAC GTT AGT CTG
1632
Pro Gln Trp Pro Pro Tyr Thr Ala Gly Ala Gln Gln Tyr Val Ser Leu
     530                       535                       540

GAC CTG CGG CCG CTG GAG GTG CGG CGG GGG CTG CGC GCC CAG GCC TGC
1680
Asp Leu Arg Pro Leu Glu Val Arg Arg Gly Leu Arg Ala Gln Ala Cys
545                       550                       555       560
```

FIGURE 4H (SEQ ID NO:1 CONTINUED)

```
GCC TTC TGG AAC CGC TTC CTC CCC AAA TTG CTC AGC GCC ACC GAC ACG
1728
Ala Phe Trp Asn Arg Phe Leu Pro Lys Leu Leu Ser Ala Thr Asp Thr
                    565                 570                 575

CTC GAC GAG GCG GAG CGC CAG TGG AAG GCC GAG TTC CAC CGC TGG AGC
1776
Leu Asp Glu Ala Glu Arg Gln Trp Lys Ala Glu Phe His Arg Trp Ser
                    580                 585                 590

TCC TAC ATG GTG CAC TGG AAG AAC CAG TTC GAC CAC TAC AGC AAG CAG
1824
Ser Tyr Met Val His Trp Lys Asn Gln Phe Asp His Tyr Ser Lys Gln
                    595                 600                 605

GAT CGC TGC TCA GAC CTG TGA
1845
Asp Arg Cys Ser Asp Leu
            610
```

FIGURE 5

```
                                                      ┌─┐
                                              ┌─┐┌─┐┌─┐│C│
                                      ┌─┐┌─┐┌─┐│C││G││G││G│┌─┐┌─┐
                              ┌─┐     │G││G││G││ ││G││G││G││ ││ │
                      ┌─┐┌─┐  │G│     │ ││ ││ ││ ││ ││ ││ ││ ││ │
              ┌─┐     │G││G│  │ │     │ ││ ││ ││ ││ ││ ││ ││ ││ │
              │C│     │ ││ │  │ │     │ ││ ││ ││ ││ ││ ││ ││ ││ │
          ┌─┐ │ │     │ ││ │  │ │     │ ││ ││ ││ ││ ││ ││ ││ ││ │
          │G│ │ │     └─┘└─┘  └─┘     └─┘└─┘└─┘└─┘└─┘└─┘└─┘└─┘└─┘
5'-TATG GAA GGA CGT GAA GAT GCA GAA CTG GTT ACC GTT CGT GGT CTT CGT GGT ATT CGC CTG
    AC  CTT CCT GCA CTT CTA CGT CTT GAC CAA TGG CAA GCA CCA GAA GCA CCA
    NdeI
                  ┌─┐┌─┐      ┌─┐        ┌─┐              ┌─┐
                  │G││C│      │C│        │G│              │G│
                  │ ││ │┌─┐   │ │┌─┐     │ │              │ │
                  └─┘└─┘│G│   └─┘│C│     └─┘              └─┘
                        └─┘      └─┘
    AAA ACT CCA GGT GGT CCT GTT TCT GCT TTT CTT GGC ATC CCC TTT GCT CTT GAA CCA CC - 3'
    TAA GCG GAC TTT TGA GGT CCA CCA GGA CAA AGA CGA AAA GAA CCG TAG GGG AAA CGA CTT GGT GGG TAC
                                                                                         NcoI
```

FIGURE 6
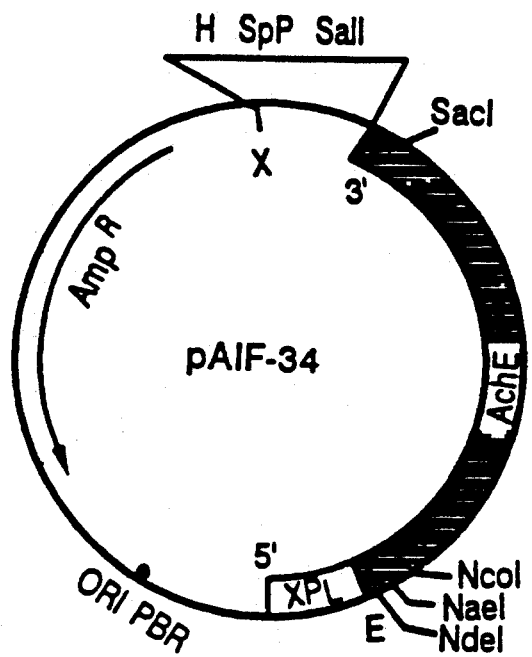
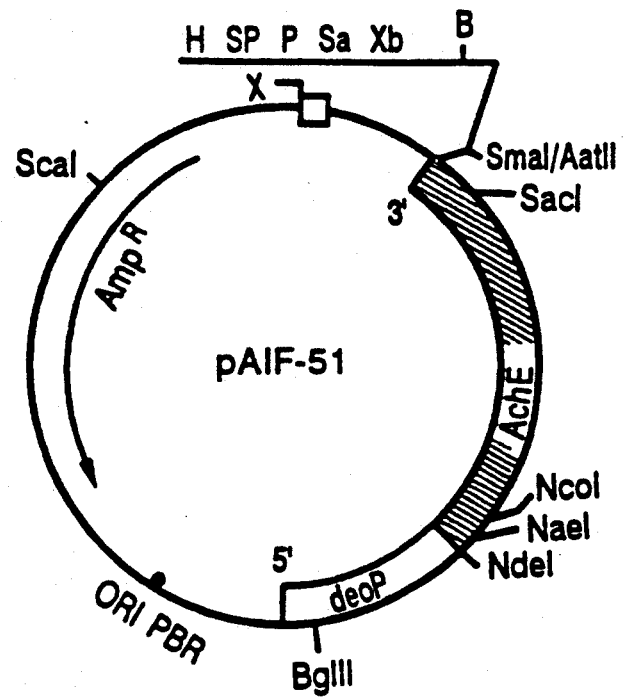

FIGURE 7
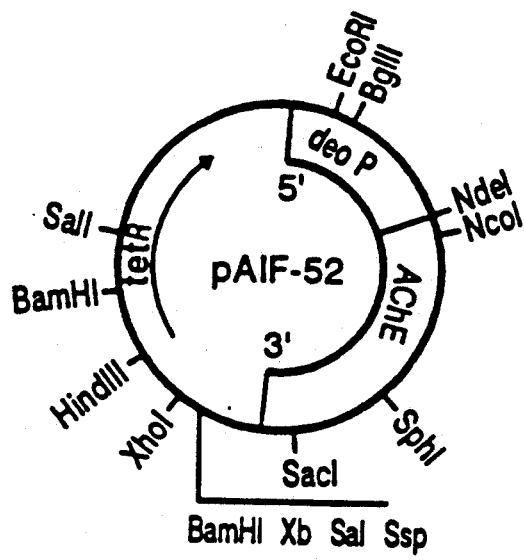
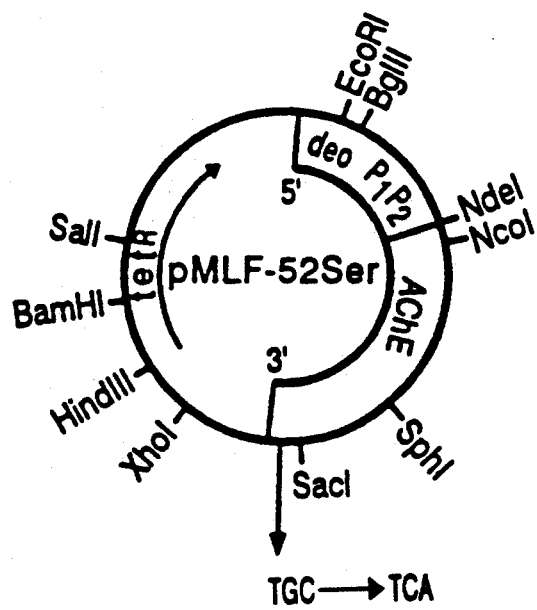

ENZYMATICALLY ACTIVE RECOMBINANT HUMAN ACETYLCHOLINESTERASE AND HOSTS AND VECTORS FOR EXPRESSION THEREOF

The invention described herein was made with government support under Contract No. DAMD 17-90-C-0107 awarded by the United States Army Medical Research Institute of Chemical Defense, Department of the Army. The U.S. Government has certain rights in this invention.

BACKGROUND OF THE INVENTION

Various publications are referenced herein. These references, in their entireties, are hereby incorporated by reference into the subject application in order to more fully describe the state of the art to which the invention relates.

The field of cholinesterases has been recently reviewed by Taylor (J. Biol. Chem., 266:4025-4028 (1991)), which is hereby incorporated by reference into this application.

The classification of cholinesterases is based on the differential specificity of the enzyme for both substrate and inhibitors. Acetylcholinesterase (AChE, EC 3.1.1.7) is preferentially active with acetylcholine and is inhibited by BW-284C51 (Koelle, G.B. (1955) J. Pharmacol. Exp. Ther. 114:167-184; Holmstedt, B. (1957) Aota. Physiol. Scand. 40: 322-330; Holmstedt, B. (1959) Pharmacol. Rev. 567-688; Silver, A. (1973) in Cholinesterases, Academic Press; and Austin, L and Berry, W.K. (1953) Biochem. J. 54: 695-700).

Studies aimed at elucidating the function of acetylcholinesterase made use of a variety of inhibitors such as physostigmine (eserine). AChE inhibitors may be used to enhance the nicotinic and muscarinic actions of acetylcholine. Some cholinesterase inhibitors are the main ingredient of insecticides used against house pests or in agriculture. Cholinesterases may have use as prophylactic or therapeutic agents in cases of organophosphate poisoning. Acetylcholinesterase (AChE) is primarily associated with nerve and muscle, typically localized at synaptic contacts. AChE, an enzyme which degrades the esters of choline, emerged as a key component in neurotransmission within the autonomic and somatic motor nervous system (Dale, H.H. (1914) J. Pharmacol. Exp. Ther. 6:147-190.). Other cholinesterases e.g. butyrylcholinesterase (BuChE, EC 3.1.1.8) are located at other sites and have other physiological functions.

Molecular species and structure of cholinesterases

Cholinesterases exist in a variety of molecular forms which differ in size, level of oligomerization, lipid content, glycosylation, collagen content and hydrodynamic properties. The catalytic subunits may be associated with a collagenlike or lipid-linked subunit which forms distinct heteromeric species. The collagen-associated enzyme consists of tetramers of catalytic subunits that are linked via disulfide bonds (Cartand, J., Bon, S. and Massoulie, J. (1978) J. Cell. Biol. 77: 315-322; Anglister, L. and Silman, I (1978) J. Mol. Biol. 125: 293-311; Rosenberry, T.L. and Richardson, J.M. (1978) Biochemistry 16: 3550-3558; and Massoulie, J. (1991) Proceedings of the 3rd International Conference on Cholinesterase (Massoulie J. et. al eds) American Chemical Society Wash. D.C. in press). The multiple collagen-like filamentous species are classified as asymmetric or A forms with a numerical subscript specifying the number of attached catalytic subunits.

The lipid containing form of AChE contains covalently attached fatty acids and is approximately 20 kD in mass (Inestrosa, N.C., Roberts, W.L., Mashal, T.L. and Rosenberry, T.L. (1978) J. Biol. Chem. 262: 4441-4444). As in the case of collagen linked subunits, the lipid moiety is attached to a tetramer of catalytic subunits.

Another species of AChE is a homomeric form that exists as dimers and tetramers of identical catalytic subunits. This form is referred to as the globular or G form. The globular form is subdivided into hydrophilic or hydrophobic G forms. These two forms differ in that a glycophospholipid is associated with hydrophobic G form (Silman, I. and Futerman, A.H. (1987) Eur. J. Biochem. 170: 11-22; Roberts, W.L., Kim, B.H. and Rosenberry T.L. (1987) Proc. Natl. Acad. Sci. U.S.A. 84: 7817-7821; and Toutant, J.P., Richards, M.K. Kroll, J.A. and Rosenberry T.L. (1990) Eur. J. Biochem. 187:31-38).

Primary structure of the cholinesterase gene family

Molecular cloning facilitated the isolation and sequence determination of cholinesterases in mammalian, lower vertebrate and invertebrate species. AChE and BuChE are both encoded by single genes, yet extensive polymorphism of the gene products has been observed (Schumacher, M. et. al. (1986) Nature 319: 407-409; Maulet, Y. et. al (1990) Neuron 4: 289-301; Arpagaus, M. et. al. (1990) Biochemistry 29:124-131; Prody, C. et. al. (1986) J. Neurosci 16: 25-35; Prody, C. et. al. (1987) Proc. Natl. Acad. Sci. USA 84: 3555-3559; and Prody, C. et. al. (1989) Proc. Natl. Acad. Sci. USA 86: 690-694). This polymorphism is a result of alternative mRNA processing of the primary gene transcript (i.e. mRNA) and post-translational modification of the polypeptide product. Comparison of the primary amino acid sequence of AChE from different sources on one hand and comparison of sequences between AChE and BuChE on the other hand reveal a high degree of homology (Maulet, Y. et. al (1990) Neuron 4: 289-301; Arpagaus, M. et. al. (1990) Biochemistry 29: 124-131; and Prody, C. et. al. (1989) Proc. Natl. Acad. Sci. USA 86: 690-694). A number of amino acid stretches which are apparently associated with the catalytic property of the enzyme have been conserved to a high degree (Doctor, B.P., et. al. (1990) FEBS Lett. 266 :123-127; Lockridge, O., et. al. (1987) J. Biol. Chem. 262: 549-557; and Chatonmet, A. and Lockridge 0. (1989) Biochem J. 260:625-634).

Cholinesterases contain varying numbers of cysteine residues: eight were reported for mature Drosophila AChE (Hall, L.M.L. and Spierer, D. (1986) EMBO J. 5: 2949-2954; and Toutant, J.P. (1989) Prog. Neurobiol. 32: 423-446), seven for Torpedo AChE, eight for mammalian BuChE (Lockridge, O., et. al. (1987) J. Biol. Chem. 262: 549-557); and seven for human AChE (Soreq, H. et al. (1990) Proc. Natl. Acad. Sci. 87: 9688-9692). These cysteinyl residues are involved in disulfide loop formation. The cysteine residue located near the C-terminus is involved in intersubunit disulfide bridge formation.

AChE and BuChE are glycosylated. The amino acid sequence that harbors the signal for glycosylation is Asn-x-Ser/Thr. The number of such sites on cholinesterase varies. For example, Toroedo AChE contains four, hBuChE contains nine (Hall, L.M.L. and Spierer, D. (1986) EMBO J. 5: 2949-2954), and Drosophila AChE contains five potential sites (Toutant, J.P. (1989) Prog. Neurobiol. 32: 423–446). The importance of glycosylation for enzyme activity has not yet been elucidated.

Cholinesterase prophylaxis against organophosphate poisoning

Organophosphate poisoning occurs most frequently among farmers upon exposure to pesticides such as malthione and parathione due to improper handling. Treatment of such poisoning calls for administration of anti-muscarinics, anti-convulsants, and oxime reactivator drugs (Gray, A.P. (1984) Drug Metab Rev. 15: 557–589).

The possibility of chemical warfare and poisoning of high density population centers by organophosphates such as soman emphasize the need to develop an effective prophylactic and therapeutic treatment.

Wolf et. al. (Wolfe, A.D. et. al. (1987) Fundam. Appl. Toxicol 9: 266–270) have shown that administration of exogenous bovine BuChE to mice prior to organophosphate exposure conferred significant protection.

Raveh et. al. (Raveh, L. et. al. (1989) Biochem. Pharmacol 38: 529–534) showed that AChE from fetal bovine serum could protect mice from 3–8 times the $LD_{50}$ concentration of MEPQ (7-methylethoxy-phosphinyloxy-1-methylquinolinium iodide). Further studies by Ashani et al (Ashani, y. el. al. (1991) Biochem. Pharmacol 41: 37–41) disclose that hBuChE administered to mice before exposure to soman could protect mice from a lethal dose without additional supportive drugs. The protective effect corresponded directly to the blood level of exogenously administered cholinesterase.

More extensive evaluation of the clinical benefit of AChE has been hindered by its limited availability.

SUMMARY OF THE INVENTION

The subject invention provides an enzymatically active, nonglycosylated, recombinant, human acetylcholinesterase comprising at least one polypeptide characterized by an amino acid sequence which is substantially identical to the amino acid sequence of naturally-occurring human acetylcholinesterase. The subject invention additionally provides an enzymatically active recombinant human acetylcholinesterase comprising at least one polypeptide characterized by an amino acid sequence in which serine is substituted for cys 611 in the sequence of naturally-occurring, human acetylcholinesterase and an enzymatically active recombinant human acetylcholinesterase comprising at least one polypeptide characterized by the presence of a methionine of the N-terminus of the amino acid sequence of naturally-occurring human acetylcholinesterase.

BRIEF DESCRIPTION OF THE FIGURES

In some of the figures abbreviations have been used for the restriction enzyme sites as follows:

A = AatII

B = BamHI

D = DraI

E = EcoRI

H = HindIII

K = KpnI

NC = NcoI

P = PstI

S or Sa = SalI

Sm = SmaI

Sp = SphI

X = XhoI

Xb = XbaI

The term "r-met-AChE" is used herein to describe authentic AChE with an additional N-terminal methionine. The term "ser/r-met-AChE" is used herein to describe a mutant of AChE containing serine at position 611 instead of the naturally-occurring cysteine.

FIG. 1. Construction of Plasmid pBR-AChE. The large fragment isolated from EcoRI digestion of plasmid pGEM-7Z(f+) was further cleaved with XhoI. The 2650 bp fragment was isolated and ligated to the large fragment isolated from EcoRI-SalI digestion of plasmid pBR322. Since SalI and XhoI are complementary, they may be ligated without any difficulty. The resulting plasmid designated pBR-AChE contains the DNA sequence encoding authentic AChE, but does not express it since it lacks a promoter and ribosomal binding site.

Figure 2:
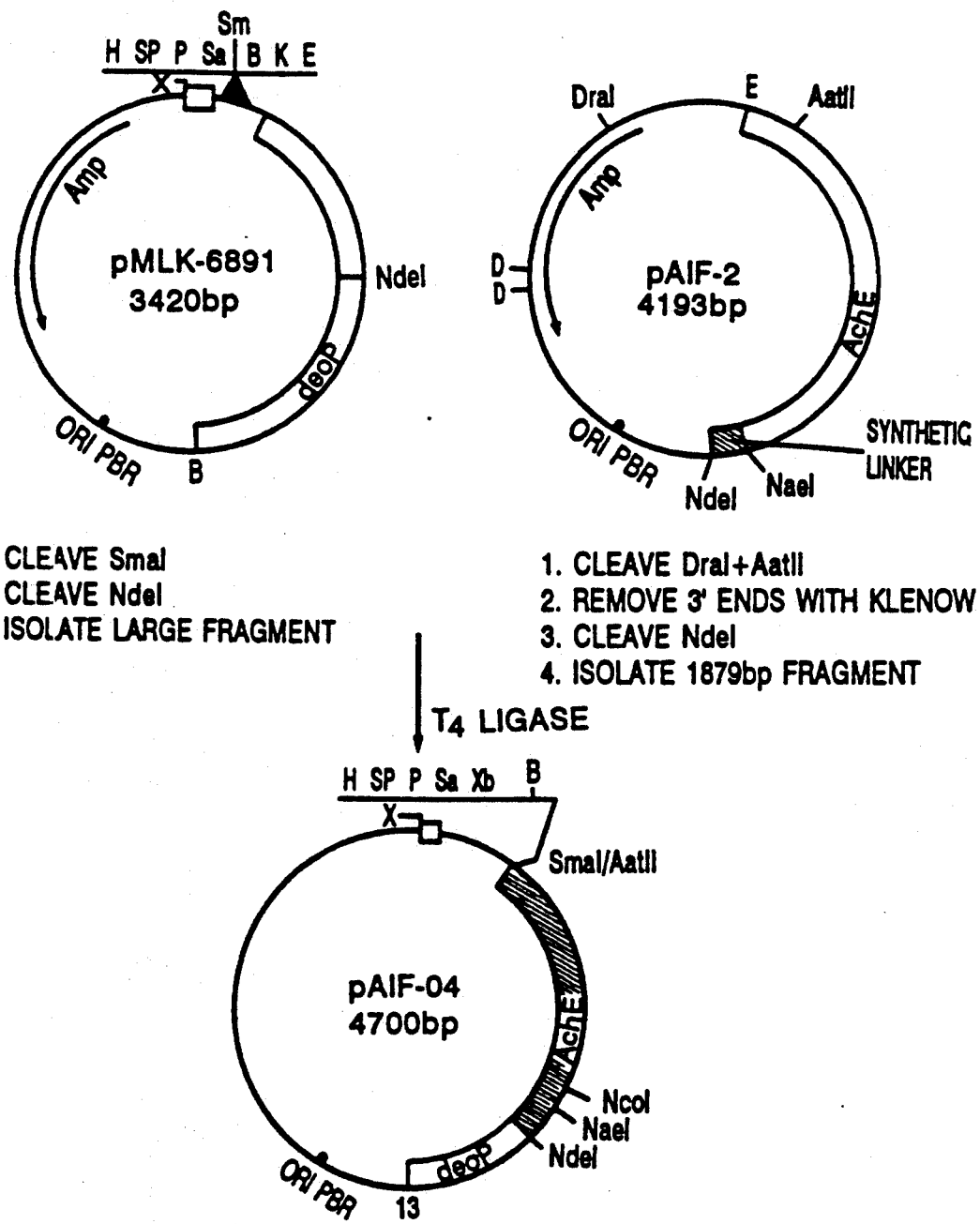

FIG. 2. Construction of plasmid pAIF-04. Plasmid pAIF-2 produced as described in Example I, was digested with DraI and AatII. The DNA was further digested with the Klenow fragment of DNA polymerase to remove the 3' ends, and then digested with NdeI. The 1879 bp fragment was isolated and ligated to the large fragment isolated from SmaI-NdeI digestion of plasmid pMLK-6891 which contains the deo promoter. The resulting expression plasmid designated pAIF-04 contains authentic AChE DNA under control of the deo P promoter, and the deo ribosomal binding site. However as described in Example 1, it failed to express AChE.

Figure 3:
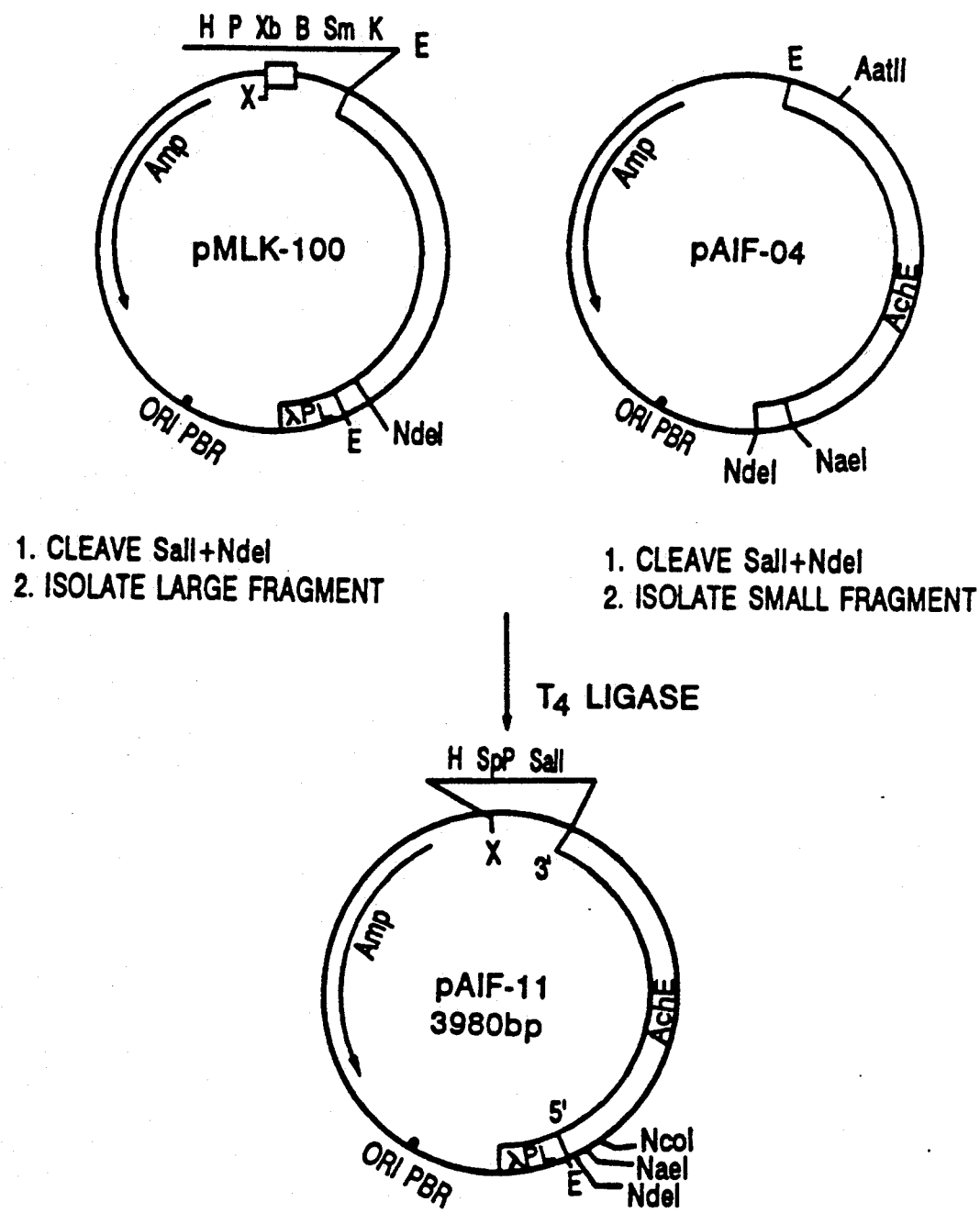

FIG. 3. Construction of Plasmid pAIF-11. The small fragment isolated from SalI-NdeI digestion of plasmid pAIF-04 was ligated to the large fragment isolated from SalI-NdeI digestion of plasmid pMLK-100 (deposited in E. coli 4300 as ATCC Accession No. 68605). The resulting expression plasmid designated pAIF-11 contained authentic AChE DNA under control of the $\lambda P_L$ promoter (and $C_{II}$ ribosomal binding site). However, as described in Example 1, it did not express AChE.

FIGS. 4A–D (SEQ ID NO:1). Sequence of Naturally Occurring Unprocessed Human AChE DNA. This figure shows the nucleotide and corresponding amino acid sequence of AChE, as disclosed by Soreq, H. et al. (1990) Proc. Natl. Acad. Sci 87:9688. The line below the amino acids shows the amino acid numbering. The nucleotide numbering is found under the second codon from the left of each row beginning with the initiator methionine. Transcription terminates at the transcription termination codon TGA immediately following the leucine residue at position 614.

Unprocessed acetylcholinesterase contains 614 amino acids.

The first 31 amino acids constitute a leader (or signal) sequence subsequently cleaved to produce mature naturally-occurring AChE containing 583 amino acids and having as N-terminus Glu$^{32}$ encoded by the GAG codon.

FIG. 5. Mutational Changes in AChE cDNA. This figure shows the GC to AT base substitutions in the two duplexes described in Example 2. The original G and C bases are in boxes in the upper row. The corresponding synthetic duplex containing the AT substitutions is recited in the lower row. These substitutions are all in the "wobble" base and do not generate changes in the amino acid encoded. The two duplexes were constructed, and joined by annealing at their complementary termini to produce a synthetic linker having a 5' NdeI site and a 3' NcoI site. Note that the mutations create several new restriction sites including an additional AatII site.

FIG. 6. Expression plasmids for AchE. Two expression plasmids were constructed as described in Example 2 with the 5' terminus of the gene modified as described in FIG. 5. Plasmid pAIF-34 expresses AChE under control of the $\lambda P_L$ promoter and $C_{II}$ ribosomal binding site, and was deposited in *E. coli* A4255 in the ATCC under Accession No. 68638. Plasmid pAIF-51 expresses AChE under control of the deo P promoter and deo ribosomal binding site.

FIG. 7. Expression Plasmids Encoding r-met-AChE and ser/r-met-AChE. Plasmid pAIF-51 was digested with XhoI, filled-in with Klenow and further digested with BglII and ScaI. The large fragment resulting was ligated to the large fragment produced by digestion of plasmid pMF5520 which had been digested with BglII and StuI. (Plasmid pMF5520 is an SOD expression plasmid which harbors the Tet$^R$ gene sequence; the construction of this plasmid is fully described in applicant's copending patent application, EPO Publication No. 303,972.)

The resulting plasmid, designated pAIF-52 expresses r-met-AChE under control of the deo P promoter. It is similar to plasmid pAIF-51 (FIG. 6) except that it is Tet$^R$ instead of Amp$^R$.

Plasmid pMLF-52ser was constructed from pAIF-52 as described in Example 4. It is identical to pAIF-52, except that the cysteine residue of position 611 (see FIGS. 4A-D and SEQ ID NO:1) was replaced by serine. Plasmid pMLF-52ser was introduced into *E. coli* S$\phi$930 and deposited in the ATCC under Accession No. 68637.

Figure 8:
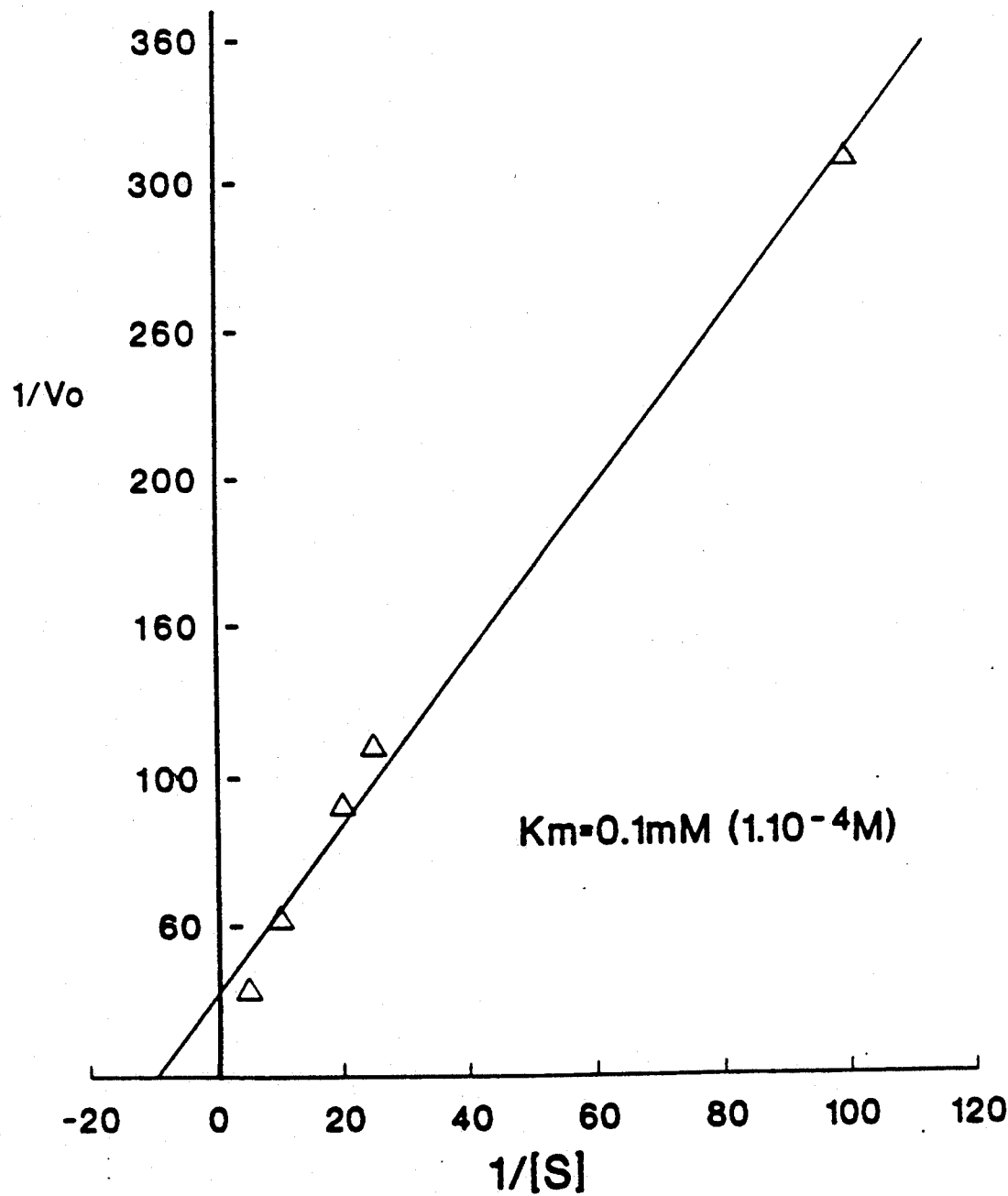

FIG. 8. Lineweaver-Burk Plot of ser/r-met-AChE Enzyme kinetics were determined for the mutant rAChE using acetylthiocholine as substrate. The results were plotted on a Lineweaver-Burk plot and the $K_m$ was calculated to be $1.0 \times 10^{-4}$.

Figure 9:
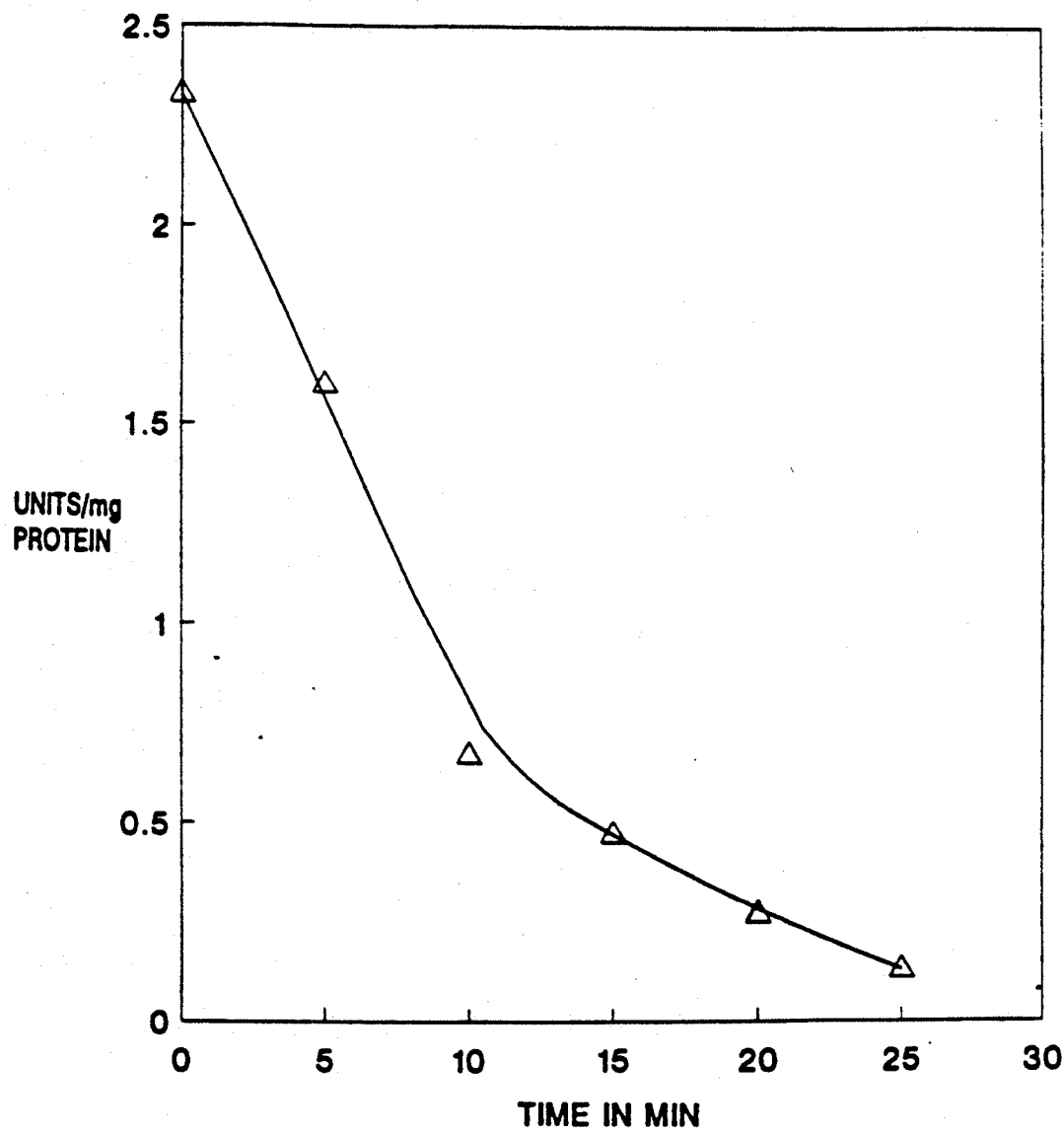

FIG. 9. Heat Inactivation of ser/r-met-AChE. This figure shows the results of heat inactivation of ser/r-met-AChE by incubation at 50° C. as described in Example 5. 50% of the activity was lost after 7 minutes, and 90% was lost after 25 minutes.

Figure 10:
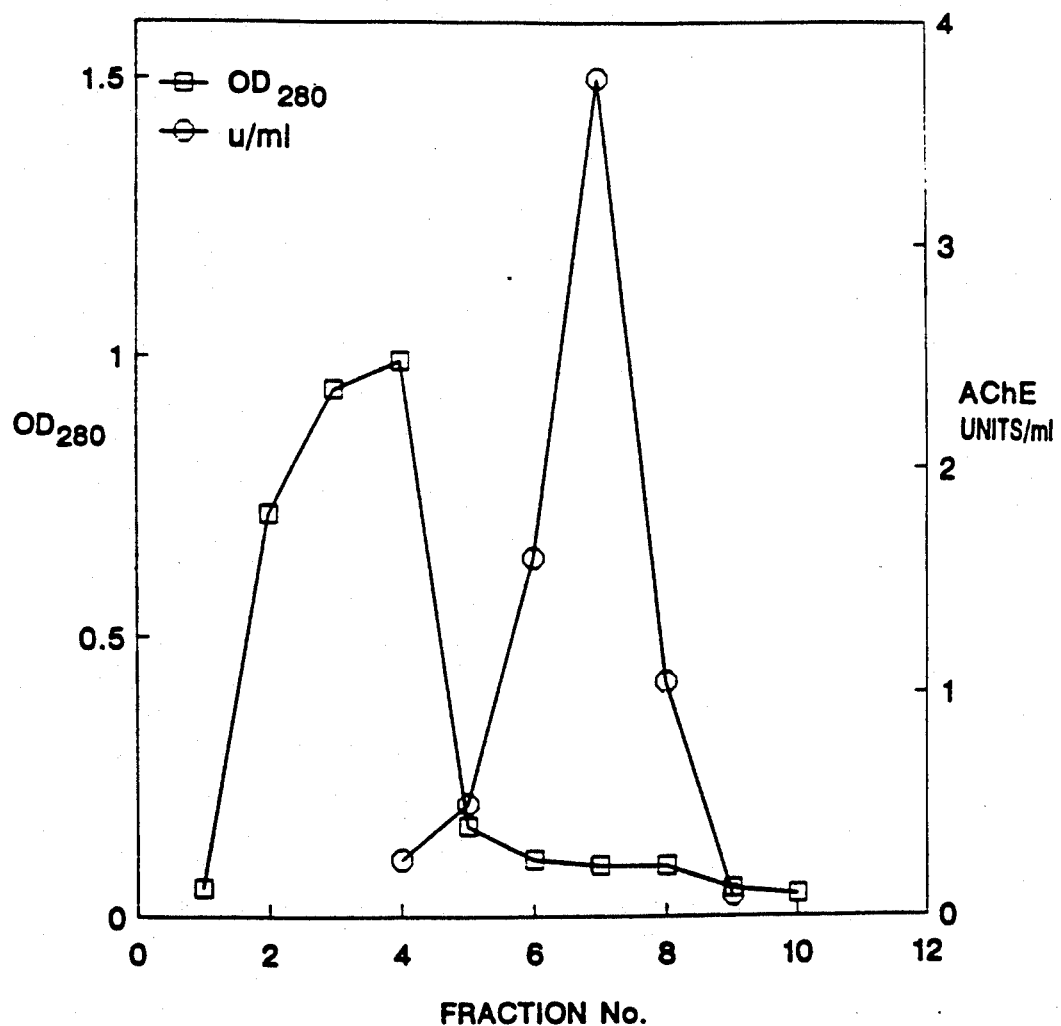

FIG. 10. Gel Filtration Chromatography of r-met-AChE. Recombinant mutant AChE was subjected to gel filtration column chromatography as described in section 5.1 of Example 4. The chromatogram shows that most of the protein is in the form of inactive aggregates which eluted in the void volume of the column. The active enzyme peak eluted in fraction 7 with a specific activity of 10.6 U/mg.

DETAILED DESCRIPTION OF THE INVENTION

The plasmids pMLF-52ser and pAIF-34 were deposited in *Escherichia coli* pursuant to, and in satisfaction of, the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession Nos. 68637 and 68638, respectively.

The subject invention provides an enzymatically active, nonglycosylated, recombinant, human acetylcholinesterase or analog thereof comprising at least one polypeptide characterized by an amino acid sequence which is substantially identical to the amino acid sequence of naturally-occurring human acetylcholinesterase.

Enzymatically active recombinant acetylcholinesterase is defined herein as having the same substrate specificity as and reactivity with molecules as that of natural acetylcholinesterase.

Analog as defined herein encompasses a polypeptide comprising the sequence of human acetylcholinesterase to which one or more amino acids have been added to either the amino terminal end, the carboxy terminal end or both, and/or to which substitutions and/or deletions to the sequence have been made, and which has the enzymatic activity of human acetylcholinesterase.

Substantially identical as defined herein encompasses the addition of fewer than four amino acids at the N-terminus of the amino acid sequence of naturally-occurring human acetylcholinesterase. Furthermore, there may be substitutions and/or deletions in the sequence which do not reduce the enzymatic activity of the polypeptide. Substitutions may encompass up to 10 residues in accordance with the homology groups described in Needleman et al., J. Mol. Biol. 48:443 (1970).

The subject invention also provides an enzymatically active human acetylcholinesterase, wherein the amino acid sequence consists essentially of the sequence of naturally occurring human acetylcholinesterase. In a preferred embodiment, a methionine is present at the N-terminus of the sequence.

The subject invention further provides the enzymatically active human acetylcholinesterases wherein serine is substituted for cys 611 in the sequence of naturally occurring, human acetylcholinesterase.

Further, the subject invention provides the enzymatically active human acetylcholinesterases comprising one polypeptide or more than one identical polypeptide. In a preferred embodiment, the enzymatically active human acetylcholinesterase or analog thereof comprises two identical polypeptides.

The subject invention provides an enzymatically active recombinant human acetylcholinesterase or analog thereof comprising at least one polypeptide characterized by an amino acid sequence in which serine is substituted for cys 611 in the sequence of naturally-occurring, human acetylcholinesterase.

The subject invention also provides an enzymatically active recombinant human acetylcholinesterase or analog thereof comprising at least one polypeptide characterized by the presence of a methionine at the N-terminus of the amino acid sequence of naturally-occurring human acetylcholinesterase. This enzymatically active human acetylcholinesterase may comprise one polypeptide or more than one identical polypeptide. In a preferred embodiment, the enzymatically active human acetylcholinesterase comprises two identical polypeptides.

The subject invention further provides an expression vector encoding any of the recombinant acetylcholinesterases described above as well as a host such as a recombinant host comprising the expression vector.

Examples of vectors that may be used to express the nucleic acid encoding the polypeptides are viruses such as bacterial viruses, e.g., bacteriophages (such as phage lambda), cosmids, plasmids, and other vectors. Genes encoding the relevant polypeptides are inserted into appropriate vectors by methods well known in the art. For example, using conventional restriction endonuclease enzyme sites, inserts and vector DNA can both be cleaved to create complementary ends which base pair with each other and are then ligated together with a DNA ligase. Alternatively, synthetic linkers harboring base sequences complementary to a restriction site in the vector DNA can be ligated to the insert DNA, which is then digested with the restriction enzyme which cuts at that site. Other means are also available.

Vectors comprising a sequence encoding the polypeptides may be adapted for expression in bacteria, yeast, or a mammalian cell which additionally comprise the regulatory elements necessary for expression of the cloned gene in the bacteria, yeast, or mammalian cells so located relative to the nucleic acid encoding the polypeptide as to permit expression thereof. Regulatory elements required for expression include promoter sequences to bind RNA polymerase, operator sequences for binding repressor molecules, and a ribosomal binding site for ribosome binding. For example, a bacterial expression vector may include a promoter-operator sequence such as $\lambda P_L O_L$ or deo promoters. For initiation of translation, the $\lambda C_{II}$ or deo ribosomal binding sites may be used. Such vectors may be obtained commercially or assembled from the sequences described by methods well known in the art, for example the methods described above for constructing vectors in general.

In addition, the subject invention provides expression plasmids encoding any of the recombinant acetylcholinesterases described above. In one embodiment, these expression plasmids are plasmids pA1F 34 deposited under ATCC Accession No. 68638 and plasmid pMLF-52ser deposited under ATCC Accession No. 68637.

Those skilled in the art will understand that the plasmids deposited in connection with this application may be readily altered by known techniques (e.g. by site-directed mutagenesis or by insertion of linkers) to encode expression of related polypeptides. Such techniques are described for example in Sambrook, J., Fritsch, E.F. and Maniatis, T. (1989) Molecular Cloning: A Laboratory Manual, 2nd edition, Cold Spring Harbor Laboratory Press.

The expression plasmids of this invention further comprise suitable regulatory elements positioned within the plasmid relative to the DNA encoding the polypeptide so as to effect expression of the polypeptide in a suitable host cell, such as promoter and operators, e.g. deo $P_1P_2$ and $\lambda P_L O_L$, ribosomal binding sites, e.g. deo and $C_{II}$, and repressors.

The suitable regulatory elements are positioned within the plasmid relative to the DNA encoding the acetylcholinesterase so as to effect expression of the acetylcholinesterase in a suitable host cell. In preferred embodiments of the invention, the regulatory elements are positioned close to and upstream of the DNA encoding the acetylcholinesterase.

The expression plasmids of this invention may be introduced into suitable host cells, preferably bacterial host cells. Preferred bacterial host cells are *Escherichia coli* cells. Examples of suitable *Escherichia coli* cells are strains S$\phi$930 or A4255, but other *Escherichia coli* strains and other bacteria can also be used as hosts for the plasmids.

The bacteria used as hosts may be any strain including auxotrophic (such as A1645), prototrophic (such as A4255), and lytic strains; F+ and F− strains; strains harboring the cI$^{857}$ repressor sequence of the λ prophage (such as A1645 and A4255); and strains devoid of the deo repressors and/or the deo gene (see European Patent Application Publication No. 0303972, published Feb. 22, 1989). *Escherichia coli* strain A4255 (F+) has been deposited under ATCC Accession No. 53468, and *Escherichia coli* strain S$\phi$930 has been deposited under ATCC Accession No. 67706.

The invention provides a bacterial cell which comprises these expression plasmids. In one embodiment, the bacterial cell is an *Escherichia coli* cell. In preferred embodiments, the invention provides an *Escherichia coli* cell containing the plasmid designated pMLF-52ser, deposited in *E. coli* strain S$\phi$930 with the ATCC under ATCC Accession No. 68637 and pAIF-34, deposited in *E. coli* strain A4255 with the ATCC under ATCC Accession No. 68638.

All the *E. coli* host strains described above can be "cured" of the plasmids they harbor by methods well-known in the art, e.g. the ethidium bromide method described by R.P. Novick in Bacteriol. Review 33, 210 (1969).

In addition, the subject invention provides a method of producing an enzymatically active recombinant human acetylcholinesterase or analog thereof comprising culturing the recombinant hosts so as to obtain expression of the recombinant acetylcholinesterase or analog thereof in the host, recovering the recombinant acetylcholinesterase or analog thereof so expressed from the host, and treating the recombinant acetylcholinesterase or analog thereof so recovered so as to obtain the enzymatically active, recombinant human acetylcholinesterase or analog thereof.

EXAMPLES

The Examples which follow are set forth to aid in understanding the invention but are not intended to, and should not be construed to, limit its scope in any way. The Examples do not include detailed descriptions of conventional methods employed in the construction of vectors and plasmids, the insertion of genes encoding polypeptides into such vectors and plasmids or the introduction of plasmids into hosts. Such methods are well known to those of ordinary skill in the art and are described in numerous publications including by way of example the following:

Sambrook, J., Fritsch, E.F. and Maniatis, T. (1989) Molecular Cloning: A Laboratory Manual, 2nd edition, Cold Spring Harbor Laboratory Press.

EXAMPLE 1

Construction of Expression Plasmids for Expression of Acetylcholinesterase

1. Introduction cDNA coding for human acetylcholinesterase has been described by Prof. H. Soreq of the Hebrew University of Jerusalem (Soreq, H. et al. (1990) Proc. Natl. Acad. Sci. 87 9688-9692 and European Patent Publication No. 388,906). Plasmid pGEM-7Z(f+) (FIG. 1), which was obtained from the U.S. Army, contains a 4 kb cDNA fragment flanked by EcoRI restriction sites, and encompasses the entire coding sequence shown in Soreq et al. The sequence coding for native acetylcholinesterase (i.e. without the leader sequence) is 1743 bp and is located on the 3' end of the 4kb fragment. Those skilled in the art may readily construct other plasmids using probes based on the sequence described by Soreq et al. Any such plasmid may serve as a useful starting point for construction of expression plasmids as hereinafter described.

Construction of plasmids 2.1. Plasmid pBR-AChE

The construction of plasmid pBR-AChE is shown in FIG. 1. The 4 kb cDNA sequence in plasmid pGEM-7Z(f+) was computer analyzed for the determination of restriction sites required to trim the 4 kb fragment so that it contains the coding sequence for mature AChE only. A unique XhoI restriction site about 750 bp upstream to the NaeI restriction site was mapped. Plasmid pGEM-7Z(f+) was then digested with EcoRI and the resulting 4 kb fragment was purified from an agarose electrophoresis gel and was digested with XhoI. The 2650 bp fragment isolated from XhoI digestion of the purified 4 kb fragment was ligated to the large fragment isolated from EcoRI-SalI digestion of plasmid pBR322. SalI and XhoI sites are complementary and can be ligated. After ligation, presence of the 2650 bp sequence in the resulting plasmid designated pBR-AChE was verified by restriction mapping. Plasmid pBR-AChE was then introduced into *E. coli* MC1061 (ATCC Accession No. 53338) by transformation.

2.2. Plasmid pAIF-2

The cloning vector, plasmid pAIF-2 (FIG. 2) was constructed as follows. Two synthetic oligomers, "A" and "B" were prepared, purified and annealed to generate the duplex shown below:

```
5' TATGGAGGGCCGGGAGGATGCAGAGCTGCTGGTGACGGTGCGTGCGTGGGGGCC 3'  A

3'         ACCTCCCGGCCCTCCTACGTCTCGACGACCACTGCCACGCACCCCCGG 5'  B
```

Plasmid pBR-AChE was digested with NdeI and NaeI. The large fragment was isolated and ligated with the synthetic duplex shown above. After transformation into *E. coli* MC1061, colonies harboring the synthetic linker were identified by hybridization on nitrocellulose filters to the synthetic radioactively labeled oligonucleotide "B" at 60° C. overnight. The filters were then washed at 60° C. with 1xSSC containing 0.1% SDS, dried, exposed to x-ray film for 3 hours, and developed. Several colonies yielding strong signals were picked and analyzed with restriction endonucleases NdeI and NaeI. One of the candidates, designated pAIF-2, was used for further manipulation. This plasmid contains the initiation codon ATG at the 5' end of the AChE gene; however it does not express AChE since it lacks a promoter and ribosomal binding site.

2.3. Construction of Plasmids Incapable of Expression

Two plasmids, one harboring the $\lambda P_L$ promoter and the other the deo P promoters were constructed in an attempt to obtain expression of AChE. (Examples of plasmids harboring the deo P1P2 promoters and deo ribosomal binding site are disclosed in coassigned EPO patent application publication No. 303972, published Feb. 22, 1989; these promotors are herein designated as the deo P promoters.) Construction of the deo plasmid is shown in FIG. 2 and was performed as follows. Plasmid pAIF-2 was first cleaved with DraI and AatII and the resulting 3' overhanging ends were removed (blunt-ended) by digestion with *E. coli* DNA polymerase large fragment (Klenow fragment). The plasmid was then digested with NdeI and a 1879 bp fragment was isolated and purified from an agarose electrophoresis gel. This fragment was then ligated to the large fragment isolated from SmaI-NdeI digestion of plasmid pMLK-6891. The ligated mix was used to transform *E. coli* MC1061. Verification that the plasmid retained the NdeI site was done by extracting the plasmid according to the method described by Birnboim et al. (Nuc. Acid. Res. 7, 1513, 1979) and cleaving with NdeI. This mini-prep plasmid extract was used to transform *E. coli* strains Sϕ732 and Sϕ930 (ATCC Accession Nos. 67362 and 67703, respectively) which are appropriate hosts for optimal expression of plasmids under control of the deo P promoter. The resulting plasmid designated pAIF-04 contained DNA encoding AChE under control of the deo promoter.

Construction of a plasmid under control of the $\lambda P_L$ promoter is shown in FIG. 3 and was performed as follows. The small fragment isolated from NdeI-SalI digestion of plasmid pAIF-04 was ligated with the large fragment isolated from SalI-NdeI digestion of the $\lambda P_L$ vector pMLK100 (deposited in *E. coli* A4300 as ATCC Accession No. 68605). The resulting plasmid which was designated pAIF-11 contains DNA encoding AChE under control of the $\lambda P_L$ promoter. This plasmid was introduced to *E. coli* A4255 (ATCC Accession No. 68456) and also to *E. coli* A4300 which both carry the temperature sensitive repressor $\lambda cI^{857}$ on the bacterial chromosome.

However as will be described below, neither plasmid pAIF-04 nor plasmid pAIF-11 was able to express AChE.

3. Attempts at Expression of AChE in Plasmids pAIF-04 and pAIF-11

*E. coli* Sϕ930 (ATCC Accession No. 67706) containing plasmid pAIF-04 was grown in 1 ml of LB+100 μg/ml ampicillin at 37° C. overnight. The culture was processed for SDS-PAGE by pelleting the cells, and suspending them in lysis buffer containing SDS. Electrophoresis was performed at room temperature for 3 hours on a 10% polyacrylamide gel to evaluate expression.

*E. coli* A4255 (ATCC Accession No. 68456) containing plasmid pAIF-11 was grown in LB+100 μg/ml ampicillin additionally containing 0.2% glucose to a cell density of $OD_{660}$ of 0.6-0.8 at 30° C. and then induced at 42° C. for a period of 1½-3 hours. Expression was evaluated on SDS-PAGE as described above.

4. Results

The cloned acetylcholinesterase gene was expected to produce a polypeptide that consists of 584 amino acids. Taking into account that the average molecular weight of an amino acid is 110, the molecular weight of a monomer of AChE was predicted to be about 62–64 kD. The electrophoretic pattern observed on 10% SDS-gels revealed a very faint band at a position corresponding to the expected molecular weight. However, this band co-migrated with a band obtained from lysates of control cultures which did not harbor an AChE insert. Although the intensity of the protein band was higher in the lane containing the extract from the expressing clones than in the lane containing the control culture, we suspected that it was not related to the desired protein product.

To further confirm this observation, total cell extracts were subjected to Western blot analysis using antibody against human erythrocyte AChE, kindly provided by Prof. H. Soreq. The results of this analysis failed to reveal a cross reactive protein band on SDS-PAGE, indicating that AChE is not expressed.

EXAMPLE 2

Construction of Plasmids for Achievement of Expression of AChE

Example 1 disclosed the construction of plasmids for achievement of expression of AChE harboring the authentic sequence as found in natural sources. As disclosed in Example 1, these plasmids were not able to express AChE.

1. Construction of Plasmids having a Modified Base Composition in the AChE DNA Gene Sequence Two synthetic DNA duplexes were prepared such that 24 base pair substitutions of GC to AT were introduced along a stretch of 130 base pairs as shown in FIG. 5. These duplexes were joined to produce a synthetic linker flanked by NdeI-NcoI restriction sites which are compatible with sites on plasmids pAIF-11 and pAIF-04. The same procedure was used in order to modify both plasmids. The synthetic linker was ligated to the large fragment isolated from NdeI-NcoI digestion of plasmids pAIF-11 or pAIF-04. The ligation of the synthetic linker with plasmid pAIF-11 resulted in plasmid pAIF-34 which expresses AChE under control of the $\lambda P_L$ promoter. Ligation of the linker with plasmid pAIF-04 resulted in plasmid pAIF-51 which expresses AChE under control of the deo P promoter. Plasmids pAIF-34 and pAIF-51 (shown in FIG. 6) were introduced into host cells *E. coli* A4255 (ATCC Accession No. 68456) and *E. coli* Sϕ930 (ATCC Accession No. 67703) respectively. *E. coli* A4255 harboring plasmid pAIF-34 was deposited in the ATCC under Accession No. 68638.

To confirm that plasmids pAIF-34 and pAIF-51 do in fact contain the modified DNA fragment between the NdeI-NcoI restriction sites, an 800 bp ScaI-SphI fragment spanning a few nucleotides upstream of the ATG initiation codon from plasmid pAIF-34 was inserted into the appropriate M13 phage and then sequenced by the Sanger dideoxy DNA sequencing method. The sequencing data confirmed that no changes other than those intended are present.

In a similar manner, plasmid pAIF-52 was cleaved with NcoI, blunt-ended with Klenow enzyme, and then cleaved with BglII. This cleavage generated a 700 bp fragment introduced into appropriate M13 DNA that was previously cleaved with BamHI and SmaI to generate compatible ends for ligation. Dideoxy DNA sequencing data obtained was identical to that obtained for pAIF-34.

Additionally, a plasmid under control of the deo P promoter was constructed containing the gene for tetracycline resistance ($Tet^R$) instead of ampicillin resistance ($Amp^R$). The resulting plasmid designated pAIF-52 contains the gene for tetracycline resistance ($Tet^R$) and modified DNA encoding authentic AChE under control of the deo P promoter (see FIG. 7). The advantage of this plasmid is its improved stability as described in section 4 below. Note that plasmids pAIF-34, pAIF-51 and pAIF-52 all encode the same authentic AChE sequence with the additional N-terminal methionine (hereinafter "r-met-AChE").

2. Expression of r-met-AChE by Plasmids having a Modified Base Composition in the AChE DNA Gene Sequence

*E. coli* A4255 harboring the $\lambda P_L$ expression plasmid pAIF-34 was grown at 30° C. to an $OD_{660}$ of 0.7 in LB medium supplemented with 100 μg/ml ampicillin and 0.2% glucose. To induce r-met-AChE synthesis, the temperature was elevated to 42° C. and the culture was grown for an additional 2-3 hours. Samples were removed at 1 hour intervals and adjusted to contain the same cell density. Total cell lysate prepared in SDS-NaOH was applied to SDS-PAGE.

*E coli* Sϕ930 harboring the deo P expression plasmid pAIF-51 was grown overnight at 37° C. in LB buffered with M9 salts medium (Miller, 1972) and supplemented with 0.1% glucose and 100 μg/ml ampicillin. The culture was harvested and processed as described above.

3. Results

Samples of the cultures were analyzed by electrophoresis on SDS polyacrylamide gels. These gels were then stained with Coomassie blue. The results showed that an intense protein band corresponding to 62kD was produced by both the $\lambda P_L$ and the deo AChE expression plasmids. This protein band comprised about 10% of total bacterial proteins and was not seen in an uninduced control culture consisting of a host which does not harbor an AChE plasmid. It is reasonable to conclude that this band is r-met-AChE produced by the plasmid.

To confirm that the protein expressed is indeed r-met-AChE, total cell lysates and fractionated material were electrophoresed on both 10% and 15% SDS-polyacrylamide gels, transferred onto nitrocellulose paper, and reacted with anti-erythrocyte AChE antiserum kindly provided by Prof. M. Soreq.

The 62 kD protein of rAChE reacted with anti-AChE antiserum prepared with AChE purified from human erythrocytes, thus confirming that the plasmids are producing rAChE, immunologically similar to naturally occurring AChE.

4. Plasmid stability

Stability of plasmids expressing high levels of any protein depend on a number of parameters characteristic to the host and plasmid. Plasmid stability was determined for *E. coli* Sϕ930 containing plasmid pAIF-51 by inoculating 200 ml buffered LB medium containing 100 μg/ml ampicillin to contain 20 cell/ml. The culture was grown at 37° C. for 16-18 hours and reached an $OD_{660}$ of 4-5. Assuming that 1 $OD_{660}$ represents about $5\times10^8$ cells/ml the number of generations from seeding to harvest is 22-25. A sample from the first culture was diluted appropriately and a new flask with 200 ml was seeded as described for the first culture. Four such successive transfers account for 100 generations. When each flask was harvested, a sample was diluted and plated on LB agar with and without ampicillin, grown overnight and colonies counted. A second fraction was saved for SDS-PAGE. A similar experiment was performed with *E. coli* A4255 containing plasmid pAIF-34.

The results of this plasmid stability study as assessed by plating and SDS-PAGE show that *E. coli* Sφ930 containing plasmid pAIF-51 maintains the plasmid for up to 45–50 generations. Samples representing generations 50–75 show a marked drop in expression that is accompanied with loss of antibiotic resistance.

No such loss was observed with hosts harboring the $\lambda P_L$ expression plasmid grown at 30° C. The lower plasmid stability of *E. coli* Sφ930 containing the deo constitutive expression plasmid pAIF-51 is attributed to the high r-met-AChE expression which interferes with plasmid replication and segregation. Furthermore, r-met-AChE is accumulated in the form of inclusion bodies which can be seen as bright blue particles within the cell during microscopic examination. Inclusion bodies tend to trap resident plasmids and thus contribute to plasmid loss. None of these factors are relevant in an inducible system such as the $\lambda P_L$ expression plasmid pAIF-34.

Similar experiments were performed with *E. coli* Sφ930 harboring plasmid pAIF-52 which contains the $Tet^R$ gene. The cells were grown in LB medium containing 10–12.5 μg/ml tetracycline and plasmid stability was monitored as described above. These cells showed plasmid stability of at least 90 generations and high level r-met-AChE production. This is in contrast to plasmid stability of less than 50 generations for plasmid pAIF-51, which contains the $Amp^R$ gene. The rationale for these differences in plasmid stability appears to be based on the biochemical properties of the two antibiotics. The β-lactamase gene confers ampicillin-resistance by producing a protein that is able to degrade ampicillin. This rapidly reduces the ampicillin concentration in the medium thus enabling plasmid-less cells to increase. The gene conferring tetracycline resistance produces a protein that prevents the antibiotic from entering the cell. Since tetracycline is not destroyed it remains active during the process and those cells that lose the plasmid become tetracycline sensitive and cannot multiply.

5. Distribution of AChE in the Host Cell

To determine if r-met-AChE is exclusively located in inclusion bodies or whether some of it is soluble, *E. coli* cells (Sφ930/AIF-51 or Sφ930/pAIF-52) were resuspended in 20 mM Tris-HCl pH 8.0 containing 10 mM EDTA, sonicated and then centrifuged. The insoluble pellet was dissolved in SDS and processed for SDS-PAGE. The electrophoretic pattern reveals that most of the r-met-AChE is indeed in the pellet which is composed of inclusion bodies. A minor fraction is apparently soluble and was noted in the supernatant of cell extracts.

EXAMPLE 3

Isolation and Partial Purification of r-met-AChE

1. Fermentation of r-met-AChE

To obtain the larger amounts of r-met-AChE necessary for purification experiments, the two *E. coli* strains described in Example 2 (i.e. Sφ930/pAIF-51 and A4255/pAIF-34) were grown in 2 liter fermentation vessels in medium composed of 10 g/l yeast extract, 20 g/l N-Z amine (casein hydrolysate) and 10–15 g/l glucose, and additionally containing 100 mg/L ampicillin or 12.5 mg/L tetracycline, depending on the strain used.

Strain Sφ930/pAIF-51 was grown at 37° C. for 10 hours and harvested at $OD_{660}=12-15$. Strain A4255-/pAIF-34 was grown in the same medium at 30° C. until $OD_{660}=10-12$ and then the temperature was raised to 42° C. for 3 hours.

2. Solubilization and Purification of Inclusion Bodies

Inclusion bodies were isolated by resuspending 5–10 g packed cells in 50 ml of 25% sucrose, 50 mM Tris-HCl pH 8.0, 10 mM EDTA and 10 μg/ml lysozyme. The cells were allowed to lyse by incubation on ice for 1–2 hours. The highly viscous extract was then sonicated intermittently for 5 minutes or until more than 90% of the cells were disrupted. The sonicated extract was centrifuged at 17 K for 30 minutes at 4° C. and the pellet resuspended in the same buffer. The pellet was washed in 4 M urea containing 20 mM Tris-HCl pH 8.0 for 30 minutes and spun at 17 K. The last wash was in $H_2O$ for 10 minutes. The final pellet was kept frozen and aliquots taken for further studies.

An aliquot of inclusion bodies in 20 mM Tris-HCl pH 8.0, 2.5 mM EDTA was adjusted to $OD_{660}$ of 40–60 and solubilized by adding 8 g of solid urea per 10 ml suspension (final concentration of 8 M urea) or in 6 M guanidine thiocyanate. The suspension was stirred for 1 hour at room temperature, centrifuged to remove undissolved particles and diluted 1:1 in 20 mM Tris-HCl pH 8.0 containing 25 mM EDTA. The clear supernatant was applied to Q-Sepharose equilibrated with 20 mM Tris-HCl pH 8.0, 2.5 mM EDTA and 4 M urea. Under these conditions many proteins bind to the resin while r-met-AChE washed through. SDS-PAGE analysis revealed that the major protein band is that of AChE. The purity of the r-met-AChE is estimated by visual judgement to be about 60–70%. The wash-through containing the r-met-AChE was then concentrated and dialyzed against 20 mM Tris-HCl pH 8.0, 2.5 mM EDTA and 10% glycerol at 4° C. The dialyzed material remained clear and was injected into a rabbit to produce anti-r-met-AChE. To substantiate the data, erythrocyte hAChE (purchased from Sigma) was also used to produce rabbit anti-AChE antiserum and confirmed the results obtained using anti-r-met-AChE antiserum.

3. Biochemical Characterization of r-met-AChE.

3.1 FPLC analysis

The partially purified r-met-AChE was subjected to gel-filtration chromatography on FPLC (Pharmacia) using Superose-12 (Pharmacia) both with and without 8 M urea. The chromatographic data suggest that most of the r-met-AChE in 8 M urea is in a form of monomer-dimer while after dialysis only multimeric forms are observed.

3.2 Solubility

Dilution of r-met-AChE in 8 M urea into 20 mM Tris-HCl pH8 buffer to a concentration greater than 500 mg/ml resulted in appreciable precipitation. Massive precipitation was also noted when r-met-AChE in 6 M guanidine was diluted in a similar manner. Incorporation of Triton X-100 or NP-40 into the denaturing solution did not prevent precipitation upon dilution.

3.3 r-met-AChE enzyme activity

Following dilution of the r-met-AChE in 8 M urea or 6 M guanidine thiocyanate, the diluted material was kept at room temperature for 2–3 hours, and then centrifuged to remove precipitates. The clear supernatant was then assayed for enzyme activity.

Enzymatic activity was determined according to Ellman (Biochem. Pharmacol. 7; 88 1961). Alternatively, a radioactive assay using $^3H$-acetylcholine iodide as substrate was implemented (Johnson, C. and Russel, R.L. Analytical Chemistry (1975) 64: 229–238). We were unable to detect enzyme activity in either case. The lack of activity could be attributed to incorrect folding of the protein or to the impurities in the partially purified material.

EXAMPLE 4

Production of Enzymatically Active r-met-AChEs

As described in Example 3, the r-met-AChE initially produced had no measurable enzymatic activity. We believed that this was due to faulty refolding/oxidation of the molecule. The development of a refolding/oxidation procedure was very arduous. The standard refolding procedures did not produce active enzyme, e.g. use of guanidine produced precipitation of the enzyme. Eventually the refolding procedure described below (in section 3) was developed which produced enzymatically active AChE; however the enzymatic activity was low.

The hAChE catalytic subunit contains 7 cysteine (Cys) residues (see FIGS. 4A–D and SEQ ID NO:1), six of which are involved in intrasubunit disulfide linkages. We considered that exchange of the C-terminal cysteine residue (position 611 of FIGS. 4A–D and SEQ ID NO:1) by an amino acid that is structurally similar to cysteine such as serine may increase the chance of proper refolding. To investigate this possibility, a plasmid was constructed that expresses a mutant of r-met-AChE containing serine at position 611 instead of the naturally-occurring cysteine (hereinafter "ser/r-met-AChE").

1. Construction of a Plasmid Expressing ser/r-met-ACh

The following synthetic oligonucleotide was prepared:

```
5'    CCTACATGGTGCACTGGAAGAACCAGTTCGACCACTACAGCAAGCAGGATC-
3'TCGAGGATGTACCACGTGACCTTCTTGGCTCAAGCTGGTGATGTCGTTCGTCCTAG-
   SacI
```

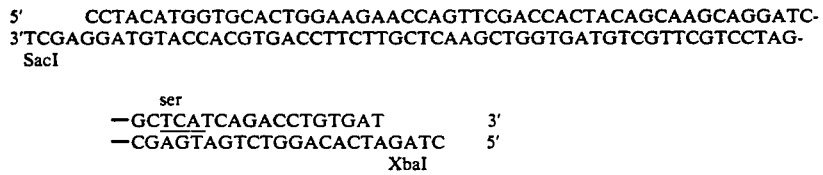

```
      ser
   -GCTCATCAGACCTGTGAT         3'
   -CGAGTAGTCTGGACACTAGATC     5'
                      XbaI
```

This synthetic linker containing a serine codon (TCA) instead of the naturally occurring cysteine codon (TGC) was prepared such that it is flanked by a SacI site at the 5' end and an XbaI site at the 3' end. The linker was ligated to the large fragment isolated from SacI-XbaI digestion of plasmid pAIF-52 (FIG. 7). The resulting plasmid encodes serine instead of cysteine at position 611 and was designated pMLF-52ser (FIG. 7). Plasmid pMLF-52ser expresses the ser/r-met-AChE polypeptide under control of the deo P promoter with a selection marker of tetracycline resistance. This plasmid was introduced to E. coli host Sφ930 by transformation and deposited in the ATCC under ATCC Accession No. 68637. It expresses ser/r-met-AChE protein at a level of about 10% of total bacterial protein.

2. Fermentation and Crude Processing

E. coli Sφ930 harboring plasmid pAIF-52 and E. coli Sφ930 harboring plasmid pMLF-52ser were each grown in a 50 L fermentation vessel to a cell density of $OD_{660}=26$–28. Both cultures were treated identically. The culture was harvested and cells disrupted in a Dyno-Mill bead mill cell disrupter. Inclusion bodies containing the r-met-AChE or ser/r-met-AChE were prepared by successive washing with 50 mM Tris-HCl pH 8.0, 1% Triton X-100, and finally with 4 M urea. Inclusion bodies were then dissolved in 8 M urea or 6 M guanidine thiocyanate containing 20 mM Tris HCl pH 8.8 for several hours and centrifuged to remove undissolved matter. The denatured AChE thus produced has no enzymatic activity. In order to obtain an enzymatically active polypeptide, the denatured enzyme must be properly refolded.

3. Refolding of rAOhEs

Crude denatured r-met-AChE or ser/r-met-AChE dissolved in 8 M urea or guanidine thiocyanate was diluted in 0.6 M arginine pH 10 containing 0.3 mM GSSG to a protein concentration of 50–200 µg/ml. (We found that the arginine could be in the range 0.1 M to 1 M, pH 8.3 to 11, and the GSSG could be in the range 0.1 mM to 0.5 mM.) This solution was stirred for 4 hours (or more) at 4° C. and then dialyzed against 10 mM HEPES pH 8.0 containing 2.5 mM EDTA or 10 mM arginine pH 10 for 16–18 hours. The dialyzed material was centrifuged at 15 K for 15 minutes and AChE activity was then assayed on the clear supernatant.

AChE activity was assayed by the spectrophotometric method of Ellman using acetylthiocholine as substrate (Ellman, G.L. et al. (1981) Biochem. Pharm. 7: 88–95)). Acetylthiocholine hydrolysis generates free thiocholine which reacts with Ellman reagent (DTNB) to produce a yellow chromophore. The concentration of the yellow chromophore is determined by the absorption at 412 nm and is proportional to the amount of AChE present. One enzyme unit (U) is the amount of enzyme which hydrolyses 1 µmole of substrate per minute. The extinction coefficient of 1 M chromophore is $13.6 \times 10^4$. Specific activity is expressed as U/mg protein. The assay solution contained 0.1 M HEPES pH 8.0 instead of 0.1 M $NaP_i$ because we found that spontaneous non-enzymatic degradation of acetylthiocholine in HEPES is much slower than in phosphate buffer.

4. Results 4.1 Comparison of recombinant AChEs

Table 1 is an example showing the recovery of active r-met-AChE and ser/r-met-AChE following in vitro refolding. Refolding of both r-met-AChE and ser/r-met-AChE was performed under identical conditions and at the same protein concentration. It is clear that GSSG enhances the recovery of active enzyme. These preliminary results suggest that activity of the ser/r-met-AChE is quantitatively many fold higher than that of the r-met-AChE having the authentic sequence. It is surprising that the activity of the mutant enzyme should be so much higher than the enzyme having the authentic sequence.

TABLE 1

| AChE Activity Following In Vitro Refolding | | | | |
|---|---|---|---|---|
| rAChE | 0.3 mM GSSG | U/ml | Protein mg/ml | Specific Activity U/mg Protein |
| r-met-AChE | − | 0.0015 | 0.267 | 0.006 |
| r-met-AChE | + | 0.0080 | 0.167 | 0.048 |
| ser/r-met- | − | 0.0654 | 0.081 | 0.807 |

TABLE 1-continued

| | AChE Activity Following In Vitro Refolding | | | |
|---|---|---|---|---|
| rAChE | 0.3 mM GSSG | U/ml | Protein mg/ml | Specific Activity U/mg Protein |
| AChE ser/r-met-AChE | + | 0.112 | 0.084 | 1.334 |

5. Improved Method of Folding and Oxidation of rAChE

As seen in Table 1, the protein obtained by the method of folding described above had a specific activity of up to 1.3 U/mg. The following procedure enables recovery of protein having much higher specific activity.

Washed inclusion bodies of ser/r-met-AChE obtained as described above were dissolved in 6 M guanidine thiocyantae, 10 mM Tris HCl pH 8.3 to a protein concentration of 3-5 µg/mL. Monomers and dimers were then separated from multimers by gel filtration on Sephacryl-400 (Pharmacia). 20-35 mg protein were loaded on the Sephacryl-400 column which had been previously equalibrated with 8 M urea, 10 mM Tris HCl pH 8.3. Protein fractions corresponding to monomers and dimers were pooled and diluted into refolding solution (0.5 M arginine pH 10.0, 0.3 mM GSSG, 0.3% PEG 4000 (polyethylene glycol), and 0.2 M tetramethylammonium chloride) to a final protein concentration of 25-50 µg/ml. After incubation at 4° C. for 24-96 hours, the solution was dialyzed against 10 mM arginine pH 10.0 for 24 hours and assayed for enzyme activity as described above. The protein concentration of the dialyzed material as determined by the Bradford protein assay was 0.026 mg/mL and had enzyme activity of 1.2 U/mL, which is specific activity of 46.2 U/mg protein. As may be seen by comparison with Table 1, this method of folding and oxidation provides protein having a much higher specific activity than was previously obtained.

EXAMPLE 5

Characterization of the Refolded rAChE Enzymes

1. $K_m$ Determination

The $K_m$ of the refolded ser/r-met-AChE as determined from a Lineweaver-Burk plot is $1.0 \times 10^{-4}$ M (FIG. 8) which is in good agreement with the value of $1.0 \times 10^{-4}$ M reported in the literature (Ellman, 1981).

Similar results were obtained for r-met-AChE.

2. Demonstration of activity by means of activity gel

It is possible to visualize AChE activity on a polyacrylamide gel. 0.04 units measured as described above of r-met-AChE and ser/r-met-AChE were applied to a 7% native polyacrylamide gel (in the absence of SDS and β-mercaptoethanol) and electrophoresed for 4 hours at room temperature at 120 V and 6-10 mA. The gel was stained according to the procedure described by Karnovsky and Roots (J. Histochem. Cytochem 12: 219-221, 1964).

Both r-met-AChE and ser/r-met-AChE, derived from Sφ930/pAIF-52 and Sφ930/pMFL-52ser respectively, generated a major activity band on the gel. The positions of the activity bands on the gel are not identical; ser/r-met-AChE migrates more slowly than r-met-AChE.

3. Heat Inactivation

Experiments were performed to determine the heat lability of ser/r-met-AChE. A solution containing the enzyme was heated to 50° C. and samples removed at 5 min intervals to determine the remaining enzyme activity. FIG. 9 shows the heat inactivation profile of ser/r-met-AChE. The plot shows that 50% of the activity is lost after 7 min and 90% of activity is lost after 25 min. This experiment confirms that the acetylcholinesterase activity being measured is due to a protein.

4. Substrate and Inhibitor Specificity of r-met-AChE and ser/r-met-AChE

The authenticity of the activity of the refolded r-met-AChE and ser/r-met-AChE was verified by testing the refolded protein with two different substrates and a specific inhibitor. Acetylthiocholine (the specific substrate), and butyrylthiocholine (the BuChE substrate), and a specific inhibitor BW-284C51 (see Background of the Invention) were tested to see whether the recombinant enzyme retained the specific characteristics of the naturally-occurring enzyme. The enzyme was assayed with each of the two substrates, or first reacted for five minutes with the specific inhibitor BW-284651 and then the specific substrate was added to the reaction mix. The results are shown in Table 2. The refolded ser/r-met-AChE showed nearly 10 times the activity towards 0.5 mM acetylthiocholine, (i.e. 0.047 U/mL) as towards 10 mM butyrylthiocholine, (i.e. 0.0044 U/mL) at the same protein concentration (0.15 mg/mL). Since the butyrylthiocholine was present at a 20-fold higher concentration than acetylthiocholine it is seen that the enzymatic activity towards the butyrylthiocholine is 200-fold less than towards the specific substrate. No activity at all was detected towards the 0.05 mM butyrylthiocholine.

Additionally, the specific inhibitor showed a strong and dose-dependent effect on the activity of the refolded ser/r-met-AChE towards the specific substrate, progressing from 57%-100% inhibition with increasing dosages from $0.8 \times 10^{-8}$ M to $0.8 \times 10^{-6}$ M.

TABLE 2

| Substrate Specificity of ser/r-met-AChE | | | | |
|---|---|---|---|---|
| Substrate or Inhibitor | U/ml | mg/ml | Specific Activity (U/mg) | % Inhibition |
| Acetylthiocholine 0.5 mM | 0.047 | 0.150 | 0.300 | |
| Butyrylthiocholine 0.5 mM | 0 | | | |
| Butyrylthiocholine 10 mM | 0.0044 | 0.150 | 0.029 | |
| BW284C51 $0.8 \times 10^{-6}$ M | 0 | — | — | 100% |
| BW284C51 $0.8 \times 10^{-7}$ M | 0.033 | — | — | 87% |
| BW284C51 $0.8 \times 10^{-8}$ M | 0.136 | — | — | 55% |
| No Inhibitor | 0.245 | — | — | — |

These results show conclusively that the refolded ser/r/met-AChE polypeptide retains the same specificities and activity as the naturally-occurring enzyme. The values presented in Tables 1 and 2 were obtained with non-purified enzyme, and may change with purified enzyme.

Similar results were obtained for r-met-AChE having the authentic sequence.

5. Effect of Detergents on Enzyme Activity of Refolded ser/r-met-AChE

The effect of several detergents on enzyme activity was also tested. 1% Triton X-100 reduced enzyme activity approximately 50%, while lauryl acid sodium salt and quaternary ammonium salts at 0.1% inhibited enzyme activity completely. This is in contrast to erythrocyte AChE, which requires Triton-X 100 for solubilization and maximum activity.

6. Partial purification of ser/r-met-AChE

A 100 ml batch of ser/r-met-AChE, refolded as described in Example 4, was concentrated to 10ml and applied to a gel filtration chromatography column of Sephacryl-200 (Pharmacia) equilibrated with 10 mM HEPES pH 8.0 2.5 mM EDTA. The column bed volume was 140 ml (in a 16 mm by 650 mm column). The flow rate was 30 ml/hr and 8 ml fractions were collected.

FIG. 10 shows the gel filtration profile. A large amount of highly aggregated material devoid of enzyme activity was recovered in the void volume. AChE activity began to be detected in fraction 4 and increased to its highest point in fraction 7. The specific activity in fraction 7 was 10.6 U/mg. SDS-PAGE analysis of fractions 6 and 7 revealed considerable levels of impurities, which may be removed by other methods such as ion-exchange chromatography. Preliminary experiments indicate that the refolded AChE binds to anion exchange columns. Note that prior to refolding, the urea-solubilized inclusion bodies which contain the AChE did not bind to ion-exchange resin.

7. Amino acid sequencing r-met-AChE obtained from Sφ930/pAIF-52 electrophoresed on SDS-PAGE was blotted onto PVDF paper and the protein band corresponding to r-met-AChE was isolated. N-terminal amino acid sequencing was carried out by the method of automated Edman degradation for the first amino acids and the sequence obtained (shown below) was found to be correct. The second row contains the single-letter amino acid notation corresponding to the sequence shown in FIGS. 4A-D (SEQ ID NO:1) from position 32 et seq (not including the initiator methionine).

Met—Glu—Gly—Arg—Glu—Asp—Ala—Glu—Leu—Leu—Val.

E—G—R—E—D—A—E—L—L—V

This is the expected sequence (see description of FIGS. 4A-D and SEQ ID NO:1). r-met-AChE expressed by plasmids pAIF-34 and pAIF-51 and ser/r-met-AChE expressed by plasmid pMLF-52ser all have the identical N-terminal sequence.

8. Conclusions

The data presented in this Example indicate that recombinant AChE expressed in *E. coli* and made enzymatically active by means of in vitro manipulation possesses properties similar to those of erythrocyte AChE. More specifically, the $K_m$, substrate specificity and inhibition by BW-284C51 of the r-met-AChE are in good agreement with those reported for the naturally-occurring enzyme. Additionally, the specific activity of ser/r-met-AChE is much higher than that of r-met-AChE having the authentic sequence. Note that the recombinant AChE is not glycosylated due to the lack of glycosylating enzymes in *E. coli*. Although glycosylation is not essential for catalytic activity, it may have a role in stabilizing the enzyme in vivo or in vitro.

Expression of enzymatically active AChE in bacteria as disclosed herein will facilitate the preparation of large amounts of the enzyme for its possible prophylactic and therapeutic use against organophosphate poisoning in human subjects. Moreover, this technology may be used to prepare modified analogs containing a strong binding site for the organophosphate poisons but devoid of the catalytic ability to hydrolyse acetylcholine.

---

What is claimed is:

1. An enzymatically active, nonglycosylated, recombinant, human acetylcholinesterase characterized by an amino acid sequence which is substantially identical to the amino acid sequence of naturally-occurring human acetylcholinesterase and wherein serine is substituted for cys$^{611}$ in the sequence of naturally occurring human acetylcholinesterase.

2. An enzymatically active, human acetylcholinesterase of claim 1, wherein a methionine is present at the N-terminus of the sequence.

3. An expression vector encoding the recombinant acetylcholinesterase of claim 1.

4. An expression plasmid of claim 3.

5. Plasmid pAIF-34.

6. Plasmid pMLF-52ser.

7. A recombinant host comprising the expression vector of claim 3.

8. A bacterial host comprising the expression plasmid of claim 4.

9. An *E. coli* host comprising the plasmid pAIF-34 (ATCC No. 68638).

10. An *E. coli* host comprising the plasmid pMLF-52ser (ATCC No. 68637).

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1845 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1842

( x i ) SEQUENCE DESCRIPTION: SEQ ID NO:1:

```
ATG  AGG  CCC  CCG  CAG  TGT  CTG  CTG  CAC  ACG  CCT  TCC  CTG  GCT  TCC  CCA        48
Met  Arg  Pro  Pro  Gln  Cys  Leu  Leu  His  Thr  Pro  Ser  Leu  Ala  Ser  Pro
 1                    5                        10                       15

CTC  CTT  CTC  CTC  CTC  CTC  TGG  CTC  CTG  GGT  GGA  GGA  GTG  GGG  GCT  GAG        96
Leu  Leu  Leu  Leu  Leu  Leu  Trp  Leu  Leu  Gly  Gly  Gly  Val  Gly  Ala  Glu
                     20                        25                       30

GGC  CGG  GAG  GAT  GCA  GAG  CTG  CTG  GTG  ACG  GTG  CGT  GGG  GGC  CGG  CTG       144
Gly  Arg  Glu  Asp  Ala  Glu  Leu  Leu  Val  Thr  Val  Arg  Gly  Gly  Arg  Leu
                     35                        40                       45

CGG  GGC  ATT  CGC  CTG  AAG  ACC  CCC  GGG  GGC  CCT  GTC  TCT  GCT  TTC  CTG       192
```

|  |  |  |  |  |  |  |  |  |  |  |  |  |  |  |  |
|---|---|---|---|---|---|---|---|---|---|---|---|---|---|---|---|
| Arg | Gly | Ile | Arg | Leu | Lys | Thr | Pro | Gly | Gly | Pro | Val | Ser | Ala | Phe | Leu |
|  | 50 |  |  |  | 55 |  |  |  |  | 60 |  |  |  |  |  |

| GGC | ATC | CCC | TTT | GCG | GAG | CCA | CCC | ATG | GGA | CCC | CGT | CGC | TTT | CTG | CCA | 240 |
|---|---|---|---|---|---|---|---|---|---|---|---|---|---|---|---|---|
| Gly | Ile | Pro | Phe | Ala | Glu | Pro | Pro | Met | Gly | Pro | Arg | Arg | Phe | Leu | Pro |  |
| 65 |  |  |  |  | 70 |  |  |  |  | 75 |  |  |  |  | 80 |  |

| CCG | GAG | CCC | AAG | CAG | CCT | TGG | TCA | GGG | GTG | GTA | GAC | GCT | ACA | ACC | TTC | 288 |
|---|---|---|---|---|---|---|---|---|---|---|---|---|---|---|---|---|
| Pro | Glu | Pro | Lys | Gln | Pro | Trp | Ser | Gly | Val | Val | Asp | Ala | Thr | Thr | Phe |  |
|  |  |  |  | 85 |  |  |  |  | 90 |  |  |  |  | 95 |  |  |

| CAG | AGT | GTC | TGC | TAC | CAA | TAT | GTG | GAC | ACC | CTA | TAC | CCA | GGT | TTT | GAG | 336 |
|---|---|---|---|---|---|---|---|---|---|---|---|---|---|---|---|---|
| Gln | Ser | Val | Cys | Tyr | Gln | Tyr | Val | Asp | Thr | Leu | Tyr | Pro | Gly | Phe | Glu |  |
|  |  |  |  | 100 |  |  |  |  | 105 |  |  |  |  | 110 |  |  |

| GGC | ACC | GAG | ATG | TGG | AAC | CCC | AAC | CGT | GAG | CTG | AGC | GAG | GAC | TGC | CTG | 384 |
|---|---|---|---|---|---|---|---|---|---|---|---|---|---|---|---|---|
| Gly | Thr | Glu | Met | Trp | Asn | Pro | Asn | Arg | Glu | Leu | Ser | Glu | Asp | Cys | Leu |  |
|  |  |  | 115 |  |  |  |  | 120 |  |  |  |  | 125 |  |  |  |

| TAC | CTC | AAC | GTG | TGG | ACA | CCA | TAC | CCC | CGG | CCT | ACA | TCC | CCC | ACC | CCT | 432 |
|---|---|---|---|---|---|---|---|---|---|---|---|---|---|---|---|---|
| Tyr | Leu | Asn | Val | Trp | Thr | Pro | Tyr | Pro | Arg | Pro | Thr | Ser | Pro | Thr | Pro |  |
| 130 |  |  |  |  | 135 |  |  |  |  | 140 |  |  |  |  |  |  |

| GTC | CTC | GTC | TGG | ATC | TAT | GGG | GGT | GGC | TTC | TAC | AGT | GGG | GCC | TCC | TCC | 480 |
|---|---|---|---|---|---|---|---|---|---|---|---|---|---|---|---|---|
| Val | Leu | Val | Trp | Ile | Tyr | Gly | Gly | Gly | Phe | Tyr | Ser | Gly | Ala | Ser | Ser |  |
| 145 |  |  |  |  | 150 |  |  |  |  | 155 |  |  |  |  | 160 |  |

| TTG | GAC | GTG | TAC | GAT | GGC | CGC | TTC | TTG | GTA | CAG | GCC | GAG | AGG | ACT | GTG | 528 |
|---|---|---|---|---|---|---|---|---|---|---|---|---|---|---|---|---|
| Leu | Asp | Val | Tyr | Asp | Gly | Arg | Phe | Leu | Val | Gln | Ala | Glu | Arg | Thr | Val |  |
|  |  |  |  | 165 |  |  |  |  | 170 |  |  |  |  | 175 |  |  |

| CTG | GTG | TCC | ATG | AAC | TAC | CGG | GTG | GGA | GCC | TTT | GGC | TTC | CTG | GCC | CTG | 576 |
|---|---|---|---|---|---|---|---|---|---|---|---|---|---|---|---|---|
| Leu | Val | Ser | Met | Asn | Tyr | Arg | Val | Gly | Ala | Phe | Gly | Phe | Leu | Ala | Leu |  |
|  |  |  | 180 |  |  |  |  | 185 |  |  |  |  | 190 |  |  |  |

| CCG | GGG | AGC | CGA | GAG | GCC | CCG | GGC | AAT | GTG | GGT | CTC | CTG | GAT | CAG | AGG | 624 |
|---|---|---|---|---|---|---|---|---|---|---|---|---|---|---|---|---|
| Pro | Gly | Ser | Arg | Glu | Ala | Pro | Gly | Asn | Val | Gly | Leu | Leu | Asp | Gln | Arg |  |
|  |  | 195 |  |  |  |  | 200 |  |  |  |  | 205 |  |  |  |  |

| CTG | GCC | CTG | CAG | TGG | GTG | CAG | GAG | AAC | GTG | GCA | GCC | TTT | GGG | GGT | GAC | 672 |
|---|---|---|---|---|---|---|---|---|---|---|---|---|---|---|---|---|
| Leu | Ala | Leu | Gln | Trp | Val | Gln | Glu | Asn | Val | Ala | Ala | Phe | Gly | Gly | Asp |  |
| 210 |  |  |  |  | 215 |  |  |  |  | 220 |  |  |  |  |  |  |

| CCG | ACA | TCA | GTG | ACG | CTG | TTT | GGG | GAG | AGC | GCG | GGA | GCC | GCC | TCG | GTG | 720 |
|---|---|---|---|---|---|---|---|---|---|---|---|---|---|---|---|---|
| Pro | Thr | Ser | Val | Thr | Leu | Phe | Gly | Glu | Ser | Ala | Gly | Ala | Ala | Ser | Val |  |
| 225 |  |  |  |  | 230 |  |  |  |  | 235 |  |  |  |  | 240 |  |

| GGC | ATG | CAC | CTG | CTG | TCC | CCG | CCC | AGC | CGG | GGC | CTG | TTC | CAC | AGG | GCC | 768 |
|---|---|---|---|---|---|---|---|---|---|---|---|---|---|---|---|---|
| Gly | Met | His | Leu | Leu | Ser | Pro | Pro | Ser | Arg | Gly | Leu | Phe | His | Arg | Ala |  |
|  |  |  |  | 245 |  |  |  |  | 250 |  |  |  |  | 255 |  |  |

| GTG | CTG | CAG | AGC | GGT | GCC | CCC | AAT | GGA | CCC | TGG | GCC | ACG | GTG | GGC | ATG | 816 |
|---|---|---|---|---|---|---|---|---|---|---|---|---|---|---|---|---|
| Val | Leu | Gln | Ser | Gly | Ala | Pro | Asn | Gly | Pro | Trp | Ala | Thr | Val | Gly | Met |  |
|  |  |  | 260 |  |  |  |  | 265 |  |  |  |  | 270 |  |  |  |

| GGA | GAG | GCC | CGT | CGC | AGG | GCC | ACG | CAG | CTG | GCC | CAC | CTT | GTG | GGC | TGT | 864 |
|---|---|---|---|---|---|---|---|---|---|---|---|---|---|---|---|---|
| Gly | Glu | Ala | Arg | Arg | Arg | Ala | Thr | Gln | Leu | Ala | His | Leu | Val | Gly | Cys |  |
|  |  | 275 |  |  |  |  | 280 |  |  |  |  | 285 |  |  |  |  |

| CCT | CCA | GGC | GGC | ACT | GGT | GGG | AAT | GAC | ACA | GAG | CTG | GTA | GCC | TGC | CTT | 912 |
|---|---|---|---|---|---|---|---|---|---|---|---|---|---|---|---|---|
| Pro | Pro | Gly | Gly | Thr | Gly | Gly | Asn | Asp | Thr | Glu | Leu | Val | Ala | Cys | Leu |  |
| 290 |  |  |  |  | 295 |  |  |  |  | 300 |  |  |  |  |  |  |

| CGG | ACA | CGA | CCA | GCG | CAG | GTC | CTG | GTG | AAC | CAC | GAA | TGG | CAC | GTG | CTG | 960 |
|---|---|---|---|---|---|---|---|---|---|---|---|---|---|---|---|---|
| Arg | Thr | Arg | Pro | Ala | Gln | Val | Leu | Val | Asn | His | Glu | Trp | His | Val | Leu |  |
| 305 |  |  |  |  | 310 |  |  |  |  | 315 |  |  |  |  | 320 |  |

| CCT | CAA | GAA | AGC | GTC | TTC | CGG | TTC | TCC | TTC | GTG | CCT | GTG | GTA | GAT | GGA | 1008 |
|---|---|---|---|---|---|---|---|---|---|---|---|---|---|---|---|---|
| Pro | Gln | Glu | Ser | Val | Phe | Arg | Phe | Ser | Phe | Val | Pro | Val | Val | Asp | Gly |  |
|  |  |  |  | 325 |  |  |  |  | 330 |  |  |  |  | 335 |  |  |

| GAC | TTC | CTC | AGT | GAC | ACC | CCA | GAG | GCC | CTC | ATC | AAC | GCG | GGA | GAC | TTC | 1056 |
|---|---|---|---|---|---|---|---|---|---|---|---|---|---|---|---|---|
| Asp | Phe | Leu | Ser | Asp | Thr | Pro | Glu | Ala | Leu | Ile | Asn | Ala | Gly | Asp | Phe |  |
|  |  |  | 340 |  |  |  |  | 345 |  |  |  |  | 350 |  |  |  |

| CAC | GGC | CTG | CAG | GTG | CTG | GTG | GGT | GTG | GTG | AAG | GAT | GAG | GGC | TCG | TAT | 1104 |
|---|---|---|---|---|---|---|---|---|---|---|---|---|---|---|---|---|
| His | Gly | Leu | Gln | Val | Leu | Val | Gly | Val | Val | Lys | Asp | Glu | Gly | Ser | Tyr |  |
|  |  | 355 |  |  |  |  | 360 |  |  |  |  | 365 |  |  |  |  |

| TTT | CTG | GTT | TAC | GGG | GCC | CCA | GGC | TTC | AGC | AAA | GAC | AAC | GAG | TCT | CTC | 1152 |
|---|---|---|---|---|---|---|---|---|---|---|---|---|---|---|---|---|
| Phe | Leu | Val | Tyr | Gly | Ala | Pro | Gly | Phe | Ser | Lys | Asp | Asn | Glu | Ser | Leu |  |
| 370 |  |  |  |  | 375 |  |  |  |  | 380 |  |  |  |  |  |  |

| | | | | | | | | | | | | | | | | |
|---|---|---|---|---|---|---|---|---|---|---|---|---|---|---|---|---|
| ATC | AGC | CGG | GCC | GAG | TTC | CTG | GCC | GGG | GTG | CGG | GTC | GGG | GTT | CCC | CAG | 1200 |
| Ile | Ser | Arg | Ala | Glu | Phe | Leu | Ala | Gly | Val | Arg | Val | Gly | Val | Pro | Gln | |
| 385 | | | | 390 | | | | | 395 | | | | | | 400 | |
| GTA | AGT | GAC | CTG | GCA | GCC | GAG | GCT | GTG | GTC | CTG | CAT | TAC | ACA | GAC | TGG | 1248 |
| Val | Ser | Asp | Leu | Ala | Ala | Glu | Ala | Val | Val | Leu | His | Tyr | Thr | Asp | Trp | |
| | | | | 405 | | | | | 410 | | | | | 415 | | |
| CTG | CAT | CCC | GAG | GAC | CCG | GCA | CGC | CTG | AGG | GAG | GCC | CTG | AGC | GAT | GTG | 1296 |
| Leu | His | Pro | Glu | Asp | Pro | Ala | Arg | Leu | Arg | Glu | Ala | Leu | Ser | Asp | Val | |
| | | | 420 | | | | | 425 | | | | | 430 | | | |
| GTG | GGC | GAC | CAC | AAT | GTC | GTG | TGC | CCC | GTG | GCC | CAG | CTG | GCT | GGG | CGA | 1344 |
| Val | Gly | Asp | His | Asn | Val | Val | Cys | Pro | Val | Ala | Gln | Leu | Ala | Gly | Arg | |
| | | | 435 | | | | 440 | | | | | 445 | | | | |
| CTG | GCT | GCC | CAG | GGT | GCC | CGG | GTC | TAC | GCC | TAC | GTC | TTT | GAA | CAC | CGT | 1392 |
| Leu | Ala | Ala | Gln | Gly | Ala | Arg | Val | Tyr | Ala | Tyr | Val | Phe | Glu | His | Arg | |
| | 450 | | | | | 455 | | | | | 460 | | | | | |
| GCT | TCC | ACG | CTC | TCC | TGG | CCC | CTG | TGG | ATG | GGG | GTG | CCC | CAC | GGC | TAC | 1440 |
| Ala | Ser | Thr | Leu | Ser | Trp | Pro | Leu | Trp | Met | Gly | Val | Pro | His | Gly | Tyr | |
| 465 | | | | | 470 | | | | | 475 | | | | | 480 | |
| GAG | ATC | GAG | TTC | ATC | TTT | GGG | ATC | CCC | CTG | GAC | CCC | TCT | CGA | AAC | TAC | 1488 |
| Glu | Ile | Glu | Phe | Ile | Phe | Gly | Ile | Pro | Leu | Asp | Pro | Ser | Arg | Asn | Tyr | |
| | | | | 485 | | | | | 490 | | | | | 495 | | |
| ACG | GCA | GAG | GAG | AAA | ATC | TTC | GCC | CAG | CGA | CTG | ATG | CGA | TAC | TGG | GCC | 1536 |
| Thr | Ala | Glu | Glu | Lys | Ile | Phe | Ala | Gln | Arg | Leu | Met | Arg | Tyr | Trp | Ala | |
| | | | 500 | | | | | 505 | | | | | 510 | | | |
| AAC | TTT | GCC | CGC | ACA | GGG | GAT | CCC | AAT | GAG | CCC | CGA | GAC | CCC | AAG | GCC | 1584 |
| Asn | Phe | Ala | Arg | Thr | Gly | Asp | Pro | Asn | Glu | Pro | Arg | Asp | Pro | Lys | Ala | |
| | | | 515 | | | | | 520 | | | | | 525 | | | |
| CCA | CAA | TGG | CCC | CCG | TAC | ACG | GCG | GGG | GCT | CAG | CAG | TAC | GTT | AGT | CTG | 1632 |
| Pro | Gln | Trp | Pro | Pro | Tyr | Thr | Ala | Gly | Ala | Gln | Gln | Tyr | Val | Ser | Leu | |
| | 530 | | | | | 535 | | | | | 540 | | | | | |
| GAC | CTG | CGG | CCG | CTG | GAG | GTG | CGG | CGG | GGG | CTG | CGC | GCC | CAG | GCC | TGC | 1680 |
| Asp | Leu | Arg | Pro | Leu | Glu | Val | Arg | Arg | Gly | Leu | Arg | Ala | Gln | Ala | Cys | |
| 545 | | | | | 550 | | | | | 555 | | | | | 560 | |
| GCC | TTC | TGG | AAC | CGC | TTC | CTC | CCC | AAA | TTG | CTC | AGC | GCC | ACC | GAC | ACG | 1728 |
| Ala | Phe | Trp | Asn | Arg | Phe | Leu | Pro | Lys | Leu | Leu | Ser | Ala | Thr | Asp | Thr | |
| | | | | 565 | | | | | 570 | | | | | 575 | | |
| CTC | GAC | GAG | GCG | GAG | CGC | CAG | TGG | AAG | GCC | GAG | TTC | CAC | CGC | TGG | AGC | 1776 |
| Leu | Asp | Glu | Ala | Glu | Arg | Gln | Trp | Lys | Ala | Glu | Phe | His | Arg | Trp | Ser | |
| | | | 580 | | | | | 585 | | | | | 590 | | | |
| TCC | TAC | ATG | GTG | CAC | TGG | AAG | AAC | CAG | TTC | GAC | CAC | TAC | AGC | AAG | CAG | 1824 |
| Ser | Tyr | Met | Val | His | Trp | Lys | Asn | Gln | Phe | Asp | His | Tyr | Ser | Lys | Gln | |
| | | | 595 | | | | | 600 | | | | | 605 | | | |
| GAT | CGC | TGC | TCA | GAC | CTG | TGA | | | | | | | | | | 1845 |
| Asp | Arg | Cys | Ser | Asp | Leu | | | | | | | | | | | |
| | 610 | | | | | | | | | | | | | | | |

( 2 ) INFORMATION FOR SEQ ID NO:2:

( i ) SEQUENCE CHARACTERISTICS:
        ( A ) LENGTH: 614 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Arg | Pro | Pro | Gln | Cys | Leu | Leu | His | Thr | Pro | Ser | Leu | Ala | Ser | Pro |
| 1 | | | | 5 | | | | | 10 | | | | | 15 | |
| Leu | Leu | Leu | Leu | Leu | Leu | Trp | Leu | Leu | Gly | Gly | Gly | Val | Gly | Ala | Glu |
| | | | 20 | | | | | 25 | | | | | 30 | | |
| Gly | Arg | Glu | Asp | Ala | Glu | Leu | Leu | Val | Thr | Val | Arg | Gly | Gly | Arg | Leu |
| | | 35 | | | | | 40 | | | | | 45 | | | |

-continued

```
Arg Gly Ile Arg Leu Lys Thr Pro Gly Gly Pro Val Ser Ala Phe Leu
    50                  55              60
Gly Ile Pro Phe Ala Glu Pro Pro Met Gly Pro Arg Arg Phe Leu Pro
 65              70              75                           80
Pro Glu Pro Lys Gln Pro Trp Ser Gly Val Val Asp Ala Thr Thr Phe
                85              90                      95
Gln Ser Val Cys Tyr Gln Tyr Val Asp Thr Leu Tyr Pro Gly Phe Glu
            100             105             110
Gly Thr Glu Met Trp Asn Pro Asn Arg Glu Leu Ser Glu Asp Cys Leu
            115             120             125
Tyr Leu Asn Val Trp Thr Pro Tyr Pro Arg Pro Thr Ser Pro Thr Pro
    130             135             140
Val Leu Val Trp Ile Tyr Gly Gly Gly Phe Tyr Ser Gly Ala Ser Ser
145             150             155                         160
Leu Asp Val Tyr Asp Gly Arg Phe Leu Val Gln Ala Glu Arg Thr Val
                165             170             175
Leu Val Ser Met Asn Tyr Arg Val Gly Ala Phe Gly Phe Leu Ala Leu
            180             185             190
Pro Gly Ser Arg Glu Ala Pro Gly Asn Val Gly Leu Leu Asp Gln Arg
            195             200             205
Leu Ala Leu Gln Trp Val Gln Glu Asn Val Ala Ala Phe Gly Gly Asp
    210             215             220
Pro Thr Ser Val Thr Leu Phe Gly Glu Ser Ala Gly Ala Ala Ser Val
225             230             235                         240
Gly Met His Leu Leu Ser Pro Pro Ser Arg Gly Leu Phe His Arg Ala
            245             250             255
Val Leu Gln Ser Gly Ala Pro Asn Gly Pro Trp Ala Thr Val Gly Met
            260             265             270
Gly Glu Ala Arg Arg Arg Ala Thr Gln Leu Ala His Leu Val Gly Cys
            275             280             285
Pro Pro Gly Gly Thr Gly Gly Asn Asp Thr Glu Leu Val Ala Cys Leu
290             295             300
Arg Thr Arg Pro Ala Gln Val Leu Val Asn His Glu Trp His Val Leu
305             310             315             320
Pro Gln Glu Ser Val Phe Arg Phe Ser Phe Val Pro Val Val Asp Gly
            325             330             335
Asp Phe Leu Ser Asp Thr Pro Glu Ala Leu Ile Asn Ala Gly Asp Phe
            340             345             350
His Gly Leu Gln Val Leu Val Gly Val Val Lys Asp Glu Gly Ser Tyr
            355             360             365
Phe Leu Val Tyr Gly Ala Pro Gly Phe Ser Lys Asp Asn Glu Ser Leu
    370             375             380
Ile Ser Arg Ala Glu Phe Leu Ala Gly Val Arg Val Gly Val Pro Gln
385             390             395             400
Val Ser Asp Leu Ala Ala Glu Ala Val Val Leu His Tyr Thr Asp Trp
            405             410             415
Leu His Pro Glu Asp Pro Ala Arg Leu Arg Glu Ala Leu Ser Asp Val
            420             425             430
Val Gly Asp His Asn Val Val Cys Pro Val Ala Gln Leu Ala Gly Arg
            435             440             445
Leu Ala Ala Gln Gly Ala Arg Val Tyr Ala Tyr Val Phe Glu His Arg
    450             455             460
Ala Ser Thr Leu Ser Trp Pro Leu Trp Met Gly Val Pro His Gly Tyr
465             470             475             480
Glu Ile Glu Phe Ile Phe Gly Ile Pro Leu Asp Pro Ser Arg Asn Tyr
```

```
                    485                              490                              495
Thr  Ala  Glu  Glu  Lys  Ile  Phe  Ala  Gln  Arg  Leu  Met  Arg  Tyr  Trp  Ala
               500                         505                    510

Asn  Phe  Ala  Arg  Thr  Gly  Asp  Pro  Asn  Glu  Pro  Arg  Asp  Pro  Lys  Ala
          515                    520                         525

Pro  Gln  Trp  Pro  Pro  Tyr  Thr  Ala  Gly  Ala  Gln  Gln  Tyr  Val  Ser  Leu
     530                         535                    540

Asp  Leu  Arg  Pro  Leu  Glu  Val  Arg  Arg  Gly  Leu  Arg  Ala  Gln  Ala  Cys
545                       550                    555                         560

Ala  Phe  Trp  Asn  Arg  Phe  Leu  Pro  Lys  Leu  Leu  Ser  Ala  Thr  Asp  Thr
               565                    570                         575

Leu  Asp  Glu  Ala  Glu  Arg  Gln  Trp  Lys  Ala  Glu  Phe  His  Arg  Trp  Ser
               580                    585                    590

Ser  Tyr  Met  Val  His  Trp  Lys  Asn  Gln  Phe  Asp  His  Tyr  Ser  Lys  Gln
          595                         600                    605

Asp  Arg  Cys  Ser  Asp  Leu
     610
```